US009114221B2

(12) United States Patent
Bacon et al.

(10) Patent No.: US 9,114,221 B2
(45) Date of Patent: Aug. 25, 2015

(54) COUNTER

(75) Inventors: Raymond Bacon, Hampshire (GB); Iain Grierson McDerment, Hertfordshire (GB)

(73) Assignee: EURO-CELTIQUE S.A., Luxembourg (LU)

( * ) Notice: Subject to any disclaimer, the term of this patent is extended or adjusted under 35 U.S.C. 154(b) by 857 days.

(21) Appl. No.: 13/138,591

(22) PCT Filed: Mar. 10, 2010

(86) PCT No.: PCT/GB2010/050404
§ 371 (c)(1),
(2), (4) Date: Jan. 19, 2012

(87) PCT Pub. No.: WO2010/103315
PCT Pub. Date: Sep. 16, 2010

(65) Prior Publication Data
US 2012/0111323 A1 May 10, 2012

(30) Foreign Application Priority Data

Mar. 10, 2009 (GB) .................................. 0904040.3

(51) Int. Cl.
*A61M 15/00* (2006.01)
*G06M 1/00* (2006.01)
(Continued)

(52) U.S. Cl.
CPC ......... *A61M 15/0065* (2013.01); *A61M 15/009* (2013.01); *A61M 15/0073* (2014.02); *G06M 1/163* (2013.01); *G06M 1/248* (2013.01)

(58) Field of Classification Search
CPC ....... G06M 1/041; G06M 1/083; G06M 1/00; G06M 1/04; G06M 1/08; G06M 1/16; G06M 1/163; G06M 1/24; G06M 1/241; G06M 1/248; A61M 15/0068; A61M 15/0073; A61M 11/00; A61M 15/00; A61M 15/0065; A61M 15/0075; A61M 15/008; A61M 15/009; B65D 55/02; B65D 55/06; B65D 55/066; B67D 5/22; G06C 27/00

USPC ............ 128/200.11–200.24, 203.15, 203.12, 128/205.23; 116/285, 299, 308, 311, 312, 116/315, 318; 222/13, 162, 28, 32, 325, 33, 222/36, 38, 402, 402.11, 402.13, 48
See application file for complete search history.

(56) References Cited

U.S. PATENT DOCUMENTS 2,002,835 A    5/1935   Rose
2,716,013 A    8/1955   Tinker
(Continued)

FOREIGN PATENT DOCUMENTS

AU         776816       7/2002
AU      2003234746      9/2003
(Continued)

OTHER PUBLICATIONS

International Search Report for PCT/GB2010/050404, mailed Sep. 27, 2010.
(Continued)

Primary Examiner — Annette Dixon
(74) Attorney, Agent, or Firm — Nixon & Vanderhye P.C.

(57) ABSTRACT

A counter containing: a first ring member having first indicia and a second ring member having second indicia, each of the first and second ring members being rotatable in increments about a common axis, one or both of the first and second indicia indicating a count; a drive mechanism for rotating the first ring member; and a coupling mechanism for releasably coupling the first ring member to the second ring member, to allow the first and second ring members to rotate cooperatively when coupled and to allow independent rotating of the first ring member when not coupled; wherein the coupling mechanism contains first and second engagement structures, the first engagement structures being movable radially outwardly and radially inwardly relative to the axis.

37 Claims, 12 Drawing Sheets

(51) Int. Cl.
*G06M 1/16* (2006.01)
*G06M 1/24* (2006.01)

(56) References Cited

U.S. PATENT DOCUMENTS

| | | | |
|---|---|---|---|
| 2,922,613 A | 6/1960 | Beecham | |
| 3,103,335 A | 9/1963 | Martinez | |
| 3,190,497 A | 6/1965 | Anthon | |
| 3,329,389 A | 7/1967 | Clark | |
| 3,598,288 A | 8/1971 | Posgate | |
| 3,746,196 A | 7/1973 | Sako | |
| 4,142,651 A | 3/1979 | Leopoldi | |
| 4,361,148 A | 11/1982 | Shackleford | |
| 4,370,368 A | 1/1983 | Hirata | |
| 4,393,106 A | 7/1983 | Maruhashi | |
| 4,486,378 A | 12/1984 | Hirata | |
| 4,576,157 A | 3/1986 | Raghuprasad | |
| 4,664,107 A | 5/1987 | Wass | |
| 4,753,371 A | 6/1988 | Michielin | |
| 4,817,822 A | 4/1989 | Rand | |
| 4,955,371 A | 9/1990 | Zamba | |
| 4,984,158 A | 1/1991 | Hillsman | |
| 5,020,527 A | 6/1991 | Dessertine | |
| 5,031,610 A | 7/1991 | Armstrong | |
| 5,042,685 A | 8/1991 | Moulding, Jr. | |
| 5,049,345 A | 9/1991 | Collette | |
| 5,069,204 A | 12/1991 | Smith | |
| 5,119,806 A | 6/1992 | Palson | |
| 5,152,456 A | 10/1992 | Ross | |
| 5,184,761 A | 2/1993 | Lee | |
| 5,193,745 A | 3/1993 | Holm | |
| 5,217,004 A | 6/1993 | Blasnik | |
| 5,239,992 A | 8/1993 | Bougamont | |
| 5,261,601 A | 11/1993 | Ross | |
| 5,273,172 A | 12/1993 | Rossbach | |
| 5,295,479 A | 3/1994 | Lankinen | |
| 5,299,701 A | 4/1994 | Barker | |
| 5,347,998 A | 9/1994 | Hodson | |
| 5,388,572 A | 2/1995 | Mulhauser | |
| 5,408,994 A | 4/1995 | Wass | |
| 5,415,161 A | 5/1995 | Ryder | |
| 5,421,482 A | 6/1995 | Garby | |
| 5,482,030 A | 1/1996 | Klein | |
| 5,487,378 A | 1/1996 | Robertson | |
| 5,501,375 A | 3/1996 | Nilson | |
| 5,511,540 A | 4/1996 | Bryant | |
| 5,544,647 A | 8/1996 | Jewett | |
| 5,544,657 A | 8/1996 | Kurowski | |
| 5,546,932 A | 8/1996 | Galli | |
| 5,549,101 A | 8/1996 | Trofast | |
| 5,549,226 A | 8/1996 | Kopp | |
| 5,564,414 A | 10/1996 | Walker | |
| 5,611,444 A | 3/1997 | Garby | |
| 5,622,163 A | 4/1997 | Jewett | |
| 5,623,920 A | 4/1997 | Bryant | |
| 5,645,050 A | 7/1997 | Zlerenberg | |
| 5,682,875 A | 11/1997 | Blower | |
| 5,692,492 A | 12/1997 | Bruna | |
| 5,718,355 A | 2/1998 | Garby | |
| 5,772,085 A | 6/1998 | Bryant | |
| 5,794,612 A | 8/1998 | Wachter | |
| 5,809,997 A | 9/1998 | Wolf | |
| 5,839,429 A | 11/1998 | Marnfeldt | |
| 5,878,917 A | 3/1999 | Reinhard | |
| 5,960,609 A | 10/1999 | Abrams | |
| 5,988,496 A | 11/1999 | Bruna | |
| 5,996,577 A | 12/1999 | Ohki | |
| 6,014,970 A | 1/2000 | Ivri | |
| 6,085,742 A | 7/2000 | Wachter | |
| 6,142,146 A | 11/2000 | Abrams | |
| 6,148,815 A | 11/2000 | Wolf | |
| 6,149,054 A | 11/2000 | Cirrillo | |
| 6,152,130 A | 11/2000 | Abrams | |
| 6,164,494 A | 12/2000 | Marelli | |
| 6,196,218 B1 | 3/2001 | Voges | |
| 6,202,642 B1 | 3/2001 | McKinnon | |
| 6,234,168 B1 * | 5/2001 | Bruna | 128/203.12 |
| 6,240,918 B1 | 6/2001 | Ambrosio | |
| 6,253,762 B1 | 7/2001 | Britto | |
| 6,260,549 B1 | 7/2001 | Sosiak | |
| 6,283,365 B1 | 9/2001 | Bason | |
| 6,318,361 B1 | 11/2001 | Sosiak | |
| 6,325,062 B1 | 12/2001 | Sosiak | |
| 6,336,453 B1 | 1/2002 | Scarrott | |
| 6,354,290 B1 | 3/2002 | Howlett | |
| 6,357,442 B1 | 3/2002 | Casper | |
| 6,360,739 B1 | 3/2002 | Rand | |
| 6,397,839 B1 | 6/2002 | Stradella | |
| 6,405,727 B1 | 6/2002 | MacMichael et al. | |
| 6,415,784 B1 | 7/2002 | Christrup | |
| 6,422,234 B1 | 7/2002 | Bacon | |
| 6,425,392 B1 | 7/2002 | Sosiak | |
| 6,427,683 B1 | 8/2002 | Drachmann | |
| 6,431,168 B1 | 8/2002 | Rand | |
| 6,435,372 B1 | 8/2002 | Blacker | |
| 6,439,227 B1 | 8/2002 | Myrman | |
| 6,443,146 B1 | 9/2002 | Voges | |
| 6,446,627 B1 | 9/2002 | Bowman | |
| 6,460,537 B1 | 10/2002 | Bryant | |
| 6,470,884 B2 | 10/2002 | Horlin | |
| 6,474,331 B1 | 11/2002 | Rand | |
| 6,510,847 B1 | 1/2003 | Helgesson | |
| 6,516,799 B1 | 2/2003 | Greenwood | |
| 6,546,928 B1 | 4/2003 | Ashurst | |
| 6,553,988 B1 | 4/2003 | Holroyd | |
| 6,581,590 B1 | 6/2003 | Genova | |
| 6,596,260 B1 | 7/2003 | Brugger | |
| 6,601,582 B2 | 8/2003 | Rand | |
| 6,615,827 B2 | 9/2003 | Greenwood | |
| 6,655,371 B2 | 12/2003 | Gallops | |
| 6,655,379 B2 | 12/2003 | Clark | |
| 6,659,307 B1 | 12/2003 | Stradella | |
| 6,672,304 B1 | 1/2004 | Casper | |
| 6,729,330 B2 | 5/2004 | Scarrott | |
| 6,745,761 B2 | 6/2004 | Christrup | |
| 6,752,145 B1 | 6/2004 | Bonney | |
| 6,752,153 B1 | 6/2004 | Eckert | |
| 6,755,190 B2 | 6/2004 | Rasmussen | |
| 6,759,108 B1 | 7/2004 | Ota | |
| 6,766,220 B2 | 7/2004 | McRae | |
| 6,805,116 B2 | 10/2004 | Hodson | |
| 6,823,863 B2 | 11/2004 | Huxham et al. | |
| 6,860,262 B2 | 3/2005 | Christrup | |
| 6,866,037 B1 | 3/2005 | Aslin | |
| 6,866,038 B2 | 3/2005 | Bacon | |
| 6,889,687 B1 | 5/2005 | Olsson | |
| 6,907,876 B1 | 6/2005 | Clark | |
| 6,926,002 B2 | 8/2005 | Scarrott | |
| 7,007,689 B2 | 3/2006 | Burns | |
| 7,036,505 B2 | 5/2006 | Bacon | |
| 7,047,964 B2 | 5/2006 | Bacon | |
| 7,047,967 B2 | 5/2006 | Knudsen | |
| 7,072,738 B2 | 7/2006 | Bonney | |
| 7,093,594 B2 | 8/2006 | Harrison | |
| 7,100,530 B2 | 9/2006 | Lu | |
| 7,107,986 B2 | 9/2006 | Rand | |
| 7,147,170 B2 | 12/2006 | Nguyen | |
| 7,167,776 B2 | 1/2007 | Maharajh | |
| 7,191,918 B2 | 3/2007 | Ouyang | |
| 7,195,134 B2 * | 3/2007 | Ouyang et al. | 222/36 |
| 7,219,664 B2 | 5/2007 | Ruckdeschel | |
| 7,225,805 B2 | 6/2007 | Bacon | |
| 7,234,460 B2 | 6/2007 | Greenleaf | |
| 7,237,727 B2 | 7/2007 | Wang | |
| 7,270,124 B2 | 9/2007 | Rasmussen | |
| 7,275,660 B2 | 10/2007 | Stradella | |
| 7,296,567 B2 | 11/2007 | Mahon | |
| 7,299,800 B2 | 11/2007 | Stradella | |
| 7,299,801 B2 | 11/2007 | Hodson | |
| 7,306,116 B2 | 12/2007 | Fuchs | |
| 7,318,434 B2 | 1/2008 | Gumaste | |
| 7,322,352 B2 * | 1/2008 | Minshull et al. | 128/203.15 |
| 7,331,340 B2 | 2/2008 | Barney | |
| 7,334,577 B2 | 2/2008 | Gumaste | |

(56) References Cited

U.S. PATENT DOCUMENTS

| Patent/Publication No. | Date | Name |
|---|---|---|
| 7,341,057 B2 | 3/2008 | Scarrott |
| 7,347,200 B2 | 3/2008 | Jones |
| 7,347,202 B2 | 3/2008 | Aslin |
| 7,367,333 B2 | 5/2008 | Hodson |
| 7,387,121 B2 | 6/2008 | Harvey |
| 7,400,940 B2 | 7/2008 | McRae |
| 7,418,961 B2 | 9/2008 | Jones |
| 7,448,342 B2 | 11/2008 | von Schuckmann |
| 7,454,267 B2 | 11/2008 | Bonney |
| 7,497,214 B2 | 3/2009 | Hodson |
| 7,510,100 B2 | 3/2009 | Stradella |
| 7,543,582 B2 * | 6/2009 | Lu et al. ............... 128/200.23 |
| 7,597,099 B2 | 10/2009 | Jones |
| 7,637,260 B2 | 12/2009 | Holroyd |
| 7,726,555 B2 * | 6/2010 | Minshull et al. ............ 235/66 |
| 7,743,765 B2 | 6/2010 | Hodson |
| 8,517,019 B2 * | 8/2013 | Brewer et al. .......... 128/205.23 |
| 2001/0013342 A1 | 8/2001 | Burns |
| 2001/0013343 A1 | 8/2001 | Andersson |
| 2001/0025639 A1 | 10/2001 | Christrup |
| 2001/0032644 A1 | 10/2001 | Hodson |
| 2002/0000225 A1 | 1/2002 | Schuler |
| 2002/0011247 A1 | 1/2002 | Ivri |
| 2002/0026938 A1 | 3/2002 | Hodson |
| 2002/0043262 A1 | 4/2002 | Langford |
| 2002/0073996 A1 | 6/2002 | O'Leary |
| 2002/0088458 A1 | 7/2002 | Christrup |
| 2002/0100473 A1 | 8/2002 | Christrup |
| 2002/0104530 A1 | 8/2002 | Ivri |
| 2002/0104532 A1 | 8/2002 | Christrup |
| 2002/0139812 A1 | 10/2002 | Scarrott |
| 2002/0189611 A1 | 12/2002 | Greenwood |
| 2003/0033055 A1 | 2/2003 | McRae |
| 2003/0065149 A1 | 4/2003 | McGinnis |
| 2003/0089368 A1 | 5/2003 | Zhao |
| 2003/0106550 A1 | 6/2003 | Harvey |
| 2003/0116155 A1 | 6/2003 | Rasmussen |
| 2003/0136401 A1 | 7/2003 | Jansen |
| 2003/0138559 A1 | 7/2003 | Ashurst |
| 2003/0150448 A1 | 8/2003 | Bacon |
| 2003/0178021 A1 | 9/2003 | Rasmussen |
| 2003/0183225 A1 | 10/2003 | Knudsen |
| 2003/0183226 A1 | 10/2003 | Brand |
| 2003/0192535 A1 | 10/2003 | Christrup |
| 2003/0207057 A1 | 11/2003 | Britto |
| 2003/0230305 A1 | 12/2003 | Christrup |
| 2004/0005475 A1 | 1/2004 | Curie |
| 2004/0020486 A1 | 2/2004 | Huxham et al. |
| 2004/0025867 A1 | 2/2004 | Holroyd |
| 2004/0025868 A1 | 2/2004 | Bruna |
| 2004/0025870 A1 | 2/2004 | Harrison |
| 2004/0055596 A1 | 3/2004 | Bacon |
| 2004/0065320 A1 | 4/2004 | Bacon |
| 2004/0065326 A1 | 4/2004 | MacMichael et al. |
| 2004/0069301 A1 | 4/2004 | Bacon |
| 2004/0079362 A1 | 4/2004 | Christrup |
| 2004/0089299 A1 | 5/2004 | Bonney |
| 2004/0107962 A1 | 6/2004 | Harrison |
| 2004/0129793 A1 | 7/2004 | Nguyen |
| 2004/0134488 A1 | 7/2004 | Davies |
| 2004/0134489 A1 | 7/2004 | Burns |
| 2004/0134824 A1 | 7/2004 | Chan |
| 2004/0139965 A1 | 7/2004 | Greenleaf |
| 2004/0139966 A1 | 7/2004 | Hodson |
| 2004/0144798 A1 | 7/2004 | Ouyang |
| 2004/0149772 A1 | 8/2004 | Ouyang |
| 2004/0149773 A1 | 8/2004 | Ouyang |
| 2004/0172162 A1 | 9/2004 | Bonney |
| 2004/0187865 A1 | 9/2004 | Ashurst |
| 2004/0230286 A1 | 11/2004 | Moore |
| 2005/0016528 A1 | 1/2005 | Aslin |
| 2005/0076904 A1 | 4/2005 | Jones |
| 2005/0081846 A1 | 4/2005 | Barney |
| 2005/0087191 A1 | 4/2005 | Morton |
| 2005/0121024 A1 | 6/2005 | Langford |
| 2005/0126469 A1 | 6/2005 | Lu |
| 2005/0143866 A1 | 6/2005 | McRae |
| 2005/0183724 A1 | 8/2005 | Gumaste |
| 2005/0205512 A1 | 9/2005 | Scarrott |
| 2005/0209558 A1 | 9/2005 | Marx |
| 2005/0263612 A1 | 12/2005 | Wang |
| 2006/0011197 A1 | 1/2006 | Hodson |
| 2006/0037611 A1 | 2/2006 | Mahon |
| 2006/0047368 A1 | 3/2006 | Maharajh |
| 2006/0060192 A1 | 3/2006 | Lu |
| 2006/0071027 A1 | 4/2006 | Davies |
| 2006/0131346 A1 | 6/2006 | Perkins |
| 2006/0151524 A1 | 7/2006 | Stradella |
| 2006/0163275 A1 | 7/2006 | Stradella |
| 2006/0174869 A1 | 8/2006 | Gumaste |
| 2006/0186223 A1 | 8/2006 | Wang |
| 2006/0213505 A1 | 9/2006 | Hodson |
| 2006/0213506 A1 | 9/2006 | Hodson |
| 2006/0213510 A1 | 9/2006 | Hodson |
| 2006/0231093 A1 | 10/2006 | Burge |
| 2006/0237002 A1 | 10/2006 | Bonney |
| 2006/0237009 A1 | 10/2006 | Jones et al. |
| 2006/0243275 A1 | 11/2006 | Ruckdeschel |
| 2006/0254581 A1 | 11/2006 | Genova |
| 2006/0278225 A1 | 12/2006 | MacMichael et al. |
| 2006/0283444 A1 | 12/2006 | Jones |
| 2006/0289005 A1 | 12/2006 | Jones et al. |
| 2006/0289008 A1 | 12/2006 | Rand |
| 2007/0017511 A1 | 1/2007 | Ohki |
| 2007/0029341 A1 | 2/2007 | Stradella |
| 2007/0051745 A1 | 3/2007 | Poulard |
| 2007/0056502 A1 | 3/2007 | Lu |
| 2007/0056580 A1 | 3/2007 | Jones |
| 2007/0056585 A1 | 3/2007 | Davies |
| 2007/0062518 A1 | 3/2007 | Geser et al. |
| 2007/0062522 A1 | 3/2007 | Bacon |
| 2007/0089735 A1 | 4/2007 | Langford |
| 2007/0119450 A1 | 5/2007 | Wharton |
| 2007/0144514 A1 | 6/2007 | Yeates |
| 2007/0163576 A1 | 7/2007 | Bacon |
| 2007/0181120 A1 | 8/2007 | Wright |
| 2007/0181123 A1 | 8/2007 | Houzego |
| 2007/0194041 A1 | 8/2007 | Stradella |
| 2007/0210102 A1 | 9/2007 | Stradella |
| 2007/0241136 A1 | 10/2007 | Poulard |
| 2007/0246042 A1 | 10/2007 | Perkins |
| 2007/0251950 A1 | 11/2007 | Bacon |
| 2007/0284383 A1 | 12/2007 | Wright |
| 2008/0017189 A1 | 1/2008 | Ruckdeschel |
| 2008/0017193 A1 | 1/2008 | Jones |
| 2008/0035144 A1 | 2/2008 | Bowman |
| 2008/0041877 A1 | 2/2008 | Stradella |
| 2008/0047556 A1 | 2/2008 | Hodson |
| 2008/0060643 A1 | 3/2008 | Hodson |
| 2008/0066742 A1 | 3/2008 | Hodson |
| 2008/0092887 A1 | 4/2008 | Hodson |
| 2008/0107848 A1 | 5/2008 | Bacon |
| 2008/0115784 A1 | 5/2008 | Gumaste |
| 2008/0135575 A1 | 6/2008 | Ingram |
| 2008/0135576 A1 | 6/2008 | Bacon |
| 2008/0173301 A1 | 7/2008 | Deaton |
| 2008/0210224 A1 | 9/2008 | Brunnberg |
| 2008/0210226 A1 * | 9/2008 | Butterworth et al. .... 128/200.17 |
| 2008/0251004 A1 | 10/2008 | Stradella |
| 2008/0283541 A1 | 11/2008 | Warby |
| 2008/0314383 A1 | 12/2008 | Barney |
| 2009/0114219 A1 | 5/2009 | Ferris |
| 2009/0211578 A1 | 8/2009 | Fletcher |
| 2009/0229604 A1 | 9/2009 | Pearson |
| 2009/0229607 A1 | 9/2009 | Brunnberg |
| 2009/0293870 A1 | 12/2009 | Brunnberg |
| 2009/0308385 A1 | 12/2009 | Brewer et al. |
| 2009/0308389 A1 | 12/2009 | Pocock |
| 2010/0012115 A1 | 1/2010 | Bacon |
| 2010/0065050 A1 | 3/2010 | Holroyd |
| 2011/0311138 A1 | 12/2011 | Williams |

(56) References Cited

U.S. PATENT DOCUMENTS

| | | | |
|---|---|---|---|
| 2012/0017900 A1 | 1/2012 | Bacon | |
| 2012/0020002 A1 | 1/2012 | Mathew | |

FOREIGN PATENT DOCUMENTS

| | | | |
|---|---|---|---|
| AU | 2003234748 | | 9/2003 |
| DE | 629163 | | 4/1936 |
| DE | 1077932 | | 3/1960 |
| DE | 8715223 | U | 2/1988 |
| DE | 4111895 | | 10/1992 |
| DE | 19745513 | | 4/1999 |
| DE | 29818662 | U | 3/2000 |
| DE | 10061723 | C | 7/2002 |
| DE | 202004021188 | U | 3/2007 |
| EP | 0428380 | B | 5/1991 |
| EP | 0501365 | | 9/1992 |
| EP | 0629563 | A | 12/1994 |
| EP | 0 764 312 | B | 4/1998 |
| EP | 1003583 | B | 5/2000 |
| EP | 1019125 | B | 7/2000 |
| EP | A-1201423 | | 5/2002 |
| EP | 1229953 | B | 8/2002 |
| EP | 1 104 318 | B | 9/2002 |
| EP | A-0820322 | | 5/2004 |
| EP | 1443997 | B | 8/2004 |
| EP | 1 065 477 | B | 5/2005 |
| EP | 1 169 245 | | 8/2006 |
| EP | 1 787 668 | B | 7/2008 |
| EP | 0883415 | B | 12/2008 |
| FR | 2654627 | | 5/1991 |
| FR | 2660630 | | 10/1991 |
| FR | 2701653 | | 8/1994 |
| GB | 161969 | | 7/1922 |
| GB | 2385640 | | 9/1945 |
| GB | 939324 | | 10/1963 |
| GB | 1026763 | | 4/1966 |
| GB | 1270272 | | 4/1972 |
| GB | 2195544 | | 4/1988 |
| GB | 2262452 | A | 6/1993 |
| GB | 2263873 | | 8/1993 |
| GB | 2264238 | A | 8/1993 |
| GB | 2266466 | A | 11/1993 |
| GB | 2278979 | B | 1/1995 |
| GB | 2278979 | B | 1/1995 |
| GB | 2279571 | A | 1/1995 |
| GB | 2292891 | A | 3/1996 |
| GB | 2 279 879 | | 10/1997 |
| GB | 2 348 928 | | 10/2000 |
| GB | 2366519 | B | 3/2002 |
| GB | 2 372 543 | | 8/2002 |
| GB | 2 372 542 | | 8/2003 |
| GB | 2398250 | A | 8/2004 |
| GB | 2398251 | A | 8/2004 |
| GB | 2 381 201 | | 2/2005 |
| GB | 2429166 | A | 2/2007 |
| GB | 2 414 187 | B | 3/2007 |
| GB | 2 448 838 | B | 2/2009 |
| JP | 56-155759 | | 12/1981 |
| JP | 57-75855 | | 5/1982 |
| JP | 63251880 | | 10/1988 |
| JP | H10-501357 | | 2/1998 |
| JP | H11-319092 | | 11/1999 |
| JP | 2003-056254 | | 2/2003 |
| JP | 2007-526562 | | 9/2007 |
| TW | I1224513 | | 12/2004 |
| WO | WO 92/07599 | | 5/1992 |
| WO | WO 92/07600 | | 5/1992 |
| WO | WO 93/03783 | | 3/1993 |
| WO | WO 93/24167 | | 12/1993 |
| WO | WO 94/05359 | | 3/1994 |
| WO | WO 94/19042 | | 9/1994 |
| WO | WO 95/08484 | | 3/1995 |
| WO | WO 96/39337 | | 12/1996 |
| WO | WO 97/11296 | | 3/1997 |
| WO | WO 97/30743 | A2 | 8/1997 |
| WO | WO 98/01822 | | 1/1998 |
| WO | WO 99/06091 | | 2/1999 |
| WO | WO 99/06092 | | 2/1999 |
| WO | WO 99/36116 | | 7/1999 |
| WO | WO 01/31578 | | 5/2001 |
| WO | WO 01/34231 | A1 | 5/2001 |
| WO | WO 01/37909 | | 5/2001 |
| WO | WO 02/16235 | | 2/2002 |
| WO | WO02/24552 | | 3/2002 |
| WO | WO 02/38207 | | 5/2002 |
| WO | WO 02/043794 | | 6/2002 |
| WO | WO 02/053295 | | 7/2002 |
| WO | WO 03/035155 | A1 | 5/2003 |
| WO | WO 03/080161 | | 10/2003 |
| WO | WO 2004/073776 | | 9/2004 |
| WO | WO 2004/089451 | | 10/2004 |
| WO | WO 2004/096329 | | 11/2004 |
| WO | WO 2005/002654 | | 1/2005 |
| WO | WO 2005/041850 | | 5/2005 |
| WO | WO 2005/111927 | | 11/2005 |
| WO | WO 2006/032971 | | 3/2006 |
| WO | WO 2006/054083 | | 5/2006 |
| WO | WO 2006/062449 | | 6/2006 |
| WO | WO 2006/119766 | | 11/2006 |
| WO | WO 2006/124517 | | 11/2006 |
| WO | WO 2007/012854 | | 2/2007 |
| WO | WO 2007/012854 | A1 | 2/2007 |
| WO | WO 2007/022898 | | 3/2007 |
| WO | WO 2007/029019 | | 3/2007 |
| WO | WO 2007/034237 | | 3/2007 |
| WO | WO 2007/066140 | | 6/2007 |
| WO | WO 2007/077450 | | 7/2007 |
| WO | WO 2007/103712 | | 9/2007 |
| WO | WO 2007/107431 | | 9/2007 |
| WO | WO 2007/141520 | | 12/2007 |
| WO | WO 2008/025087 | | 3/2008 |
| WO | WO 2008/040772 | | 4/2008 |
| WO | WO 2008/079350 | | 7/2008 |
| WO | WO 2008/079360 | | 7/2008 |
| WO | WO 2008/087369 | | 7/2008 |
| WO | WO 2008/104366 | | 9/2008 |
| WO | WO 2008/119552 | | 10/2008 |
| WO | WO 2008/148864 | | 12/2008 |

OTHER PUBLICATIONS

Written Opinion of the International Searching Authority for PCT/GB2010/050404, mailed Sep. 27, 2010.

Rejection Decision dated Feb. 25, 2011, from copending Japanese Application No. 2007-547614, citing JP 57-75855 and JP 56-155759 (one page).

"Polyethylene-linear low density (LLDPE) CAS No. 9002-88-4" http://www.icis.com/v2/chemicals/9076159/polvethvlene-linear-low-densitv.html (Jan. 19, 2011).

Japanese Office Action dated Sep. 24, 2010, issued in corresponding Japanese Application No. 2007-547614 (in English)—6 pages.

International Search Report for PCT/GB2005/004834 mailed May 2, 2006.

Definition of "mouth"; http://www.merriam-webster.com/dictionary/mouth; 2011.

English translation of the Office Action, dated Jan. 19, 2015, issued in connection with Japanese Patent Application No. 2013-096218 (Euro-Celtique SA).

* cited by examiner

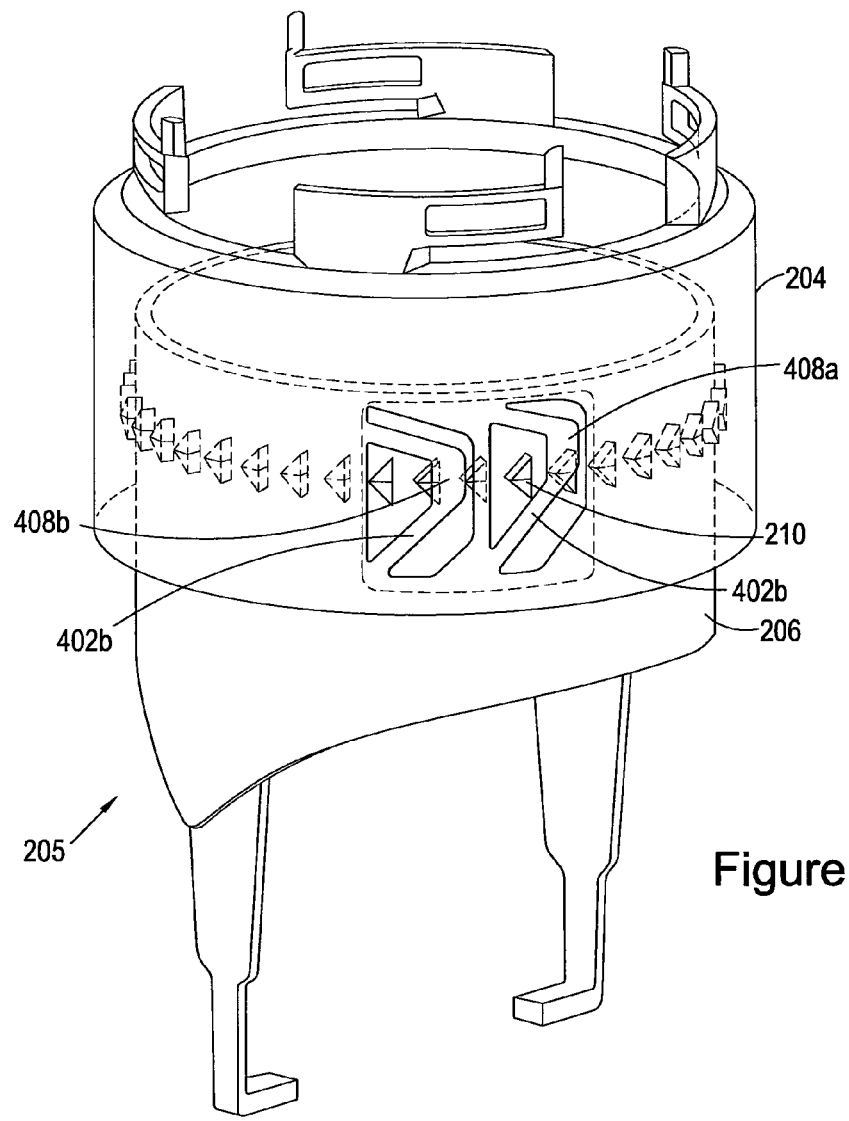
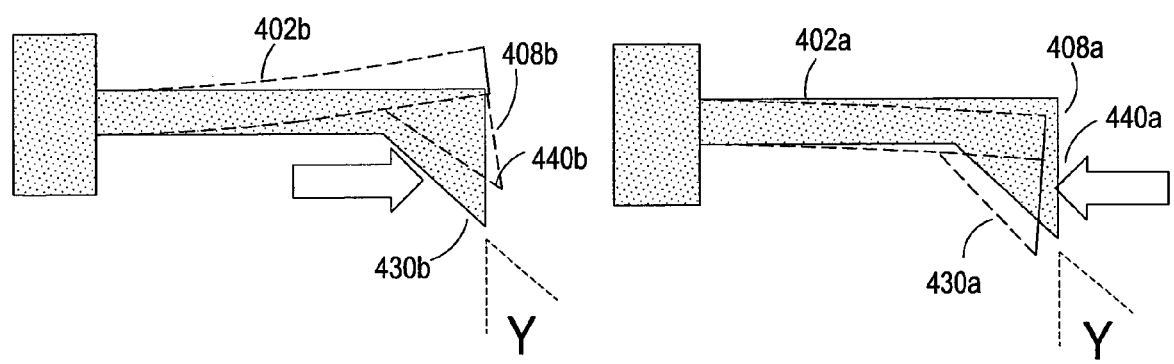
Figure 7A
Figure 7B

COUNTER

This application is the U.S. national phase of International Application No. PCT/GB2010/050404, filed 10 Mar. 2010, which designated the U.S. and claims priority to GB Application No. 0904040.3, filed 10 Mar. 2009, the entire contents of each of which are hereby incorporated by reference.

FIELD OF THE INVENTION

This invention generally relates to counters and in particular to counters for use with dispensers and to dispensers comprising said counters. More particularly the present invention relates to counters for use with metered-dose dispensers, such as metered-dose inhalers (MDIs).

BACKGROUND OF THE INVENTION

Counters are useful in a wide variety of applications, and are especially important in the field of medical dispensers where an accurate determination of the number of doses of medicament remaining in a medicament container might otherwise be difficult to obtain. An example of such a medical dispenser is a metered-dose inhaler.

Metered-dose inhalers (MDIs) are devices for dispensing medicaments, e.g. in aerosol form, to the lungs. Broadly speaking dispensers such as MDIs are comprised of two components: a container and a delivery device. The container holds the medication, e.g. dissolved or suspended in a propellant under high pressure to maintain a liquid phase. Additionally the container often comprises an internal metering valve, which is designed to release a precisely measured, reproducible dose of medicament when the valve is actuated. The delivery device typically includes an actuator and a mouthpiece. The actuator, which can be triggered by the user, for example by inhalation or manual operation, typically interacts with the metering valve of the container to induce release of a dose. The mouthpiece serves to direct the medication towards the user. FIG. 1 provides a view of a breath actuated dispenser and will be discussed in more detail below.

As medicament containers are typically made of an opaque material such as aluminium, and may be housed entirely within a delivery device, it is generally not possible for a user to gauge effectively how many doses of medicament remain therein. This may result in a user prematurely discarding a MDI still containing doses of medicament or worse using the MDI beyond its recommended lifetime. Neither situation is desirable—the former is wasteful while the latter is potentially dangerous. Users sometimes shake MDIs to try to obtain a measure of whether any medicament is present therein, but this only provides a very crude qualitative measure of the container contents. It would not, for example, enable a user to distinguish between a container comprising enough medicament and propellant to form a dose and one comprising a quantity of medicament and propellant that is less than that needed to fill the metering valve. In other words, there is a risk that users overestimate the amount of medicament present in a container and mistakenly conclude that there is sufficient medicament remaining for another dose when in fact there is not. Additionally a user may not be provided with sufficient warning to obtain a replacement medicament container prior to the one in use running out.

It is therefore desirable to provide dispensers, e.g. inhalers, with a counter mechanism that enables a user to track how many doses have been dispensed therefrom and, complementarily, how many doses remain. Indeed, regulatory bodies such as the Food and Drug Administration (FDA) of the United States and the European Medicines Agency (EMEA) have issued guidelines encouraging the implementation of dose-counters (Food and Drug Administration, "Guidance for industry: integration of dose counting mechanisms into MDI drug products", 2003; European Agency for Evaluation of Medicinal Products, "Final guideline on the quality of inhalation and nasal products", 2005).

Dose counters can generally be classified according to the manner by which a 'count' is registered, these being mechanical counters comprised of a series of moving parts that respond to a movement or mechanical force resulting, for example, in a displacement of the container/housing; electronic counters having electrical circuitry to sense an event associated with an actuation such as sound, temperature or pressure change; and electro-mechanical counters which combine electrical and mechanical parts.

Some background prior art relating to dose counters includes: EP1169245 Dispensing Apparatus Comprising a Dosage Counting Device; PCT/GB97/03480 Inhaler Dose Counter; PCT/US1996/008418 Indicator Device Responsive to Axial Force; PCT/FR2004/001844 Improved Dose Indicator for Fluid Product Dispensing Device; GB2372542 Dosage Counting Device; PCT/CA04/001884 Indicating Device with Warning Dosage Indicator; PCT/US04/039926 Dose Counter for Dispensers; and U.S. Pat. No. 7,047,964 Dispenser for Medicament.

Other developments in the field of dose counters include Bang & Olufsen Medicom's 'Insulair' (Trade Mark) device, and the disclosures of: WO 98/056444 Dispenser with Doses Counter; WO 04/001664 Actuation Indicator for a Dispensing Device; WO 07/012,854 Canister-Supported Rotating Ring Count Readout Assembly for a Metered Dose Inhaler; and DE 10061723 Zählwerk zum Zählen dosierter Abgaben flüssiger oder fester Produkte sowie Einrichtung zum dosierten Abgeben solcher Produkte.

Although such devices have provided the advantage of being able to provide some measure of the number of doses of medicament dispensed from a container and/or the number of doses remaining therein, there remains room for improvement. In particular it has proven difficult to provide dose counters that reliably "count" the release of medicament doses from containers. The difficulty encountered is that a relatively small movement, typically of the metering valve stem, needs to be detected and translated into a count. This difficulty is exacerbated by the fact that manufacturing tolerances in the length of medicament containers means they do not have a consistent length. At the same time, it is highly undesirable for any movements to not be counted since this will lead to the counter indicating a higher number of doses remaining than is actually the case. Moreover there is also regulatory pressure to minimise the number of false counts.

Additionally it is desirable that a counter, especially a medicament dose counter, display the count information in an easy to read form so it may be used by children and the elderly as well as adults. Naturally there is also a need that the counter can be manufactured at low cost.

SUMMARY OF THE INVENTION

According to a first aspect of the invention there is therefore provided a counter comprising:
a first ring member having first indicia and a second ring member having second indicia, each of said first and second ring members being rotatable in increments about a common axis, one or both of said first and second indicia indicating a count; and a drive mechanism for rotating said first ring member and for rotating the second ring member after one or more predetermined degrees of rotation of the first ring member. Preferably the rotations serve to provide a predetermined alignment of said first and second indicia.

In a preferred embodiment the counter further comprises a coupling mechanism for releasably coupling said first ring member to said second ring member, to allow said first and second ring members to rotate cooperatively when coupled and to allow independent rotating of said first ring member when not coupled.

In a particularly preferred embodiment the coupling mechanism comprises first and second engagement means, said first engagement means being movable radially outwardly and radially inwardly relative to said axis.

Thus in a further aspect the present invention provides a counter comprising:
a first ring member having first indicia and a second ring member having second indicia, each of said first and second ring members being rotatable in increments about a common axis, one or both of said first and second indicia indicating a count;
a drive mechanism for rotating said first ring member; and
a coupling mechanism for releasably coupling said first ring member to said second ring member, to allow said first and second ring members to rotate cooperatively when coupled and to allow independent rotating of said first ring member when not coupled;
wherein said coupling mechanism comprises first and second engagement means, said first engagement means being movable radially outwardly and radially inwardly relative to said axis.

A skilled person will understand that in this context "movable" is to be interpreted broadly as including any suitable movement/displacement such as a bending, flexing, tilting, pivoting and/or shifting movement. However, in preferred embodiments the first engagement means is deflectable radially outwardly to engage with said second engagement means. Thus, the coupling mechanism preferably includes a deflector to deflect the first engagement means radially outwardly. The deflector may be in a fixed position relative to the rotating first and second ring members. Preferably the deflector is attached to a medicament container or a housing surrounding said container.

In preferred embodiments the first engagement means is deflected radially outwardly after a predetermined degree or amount of rotation of the first ring member. The predetermined amount of rotation of the first ring member is associated with less than a full rotation of the first ring member about the common axis, for example a quarter rotation of the first ring member about the common axis. However, other arrangements may equally be implemented such as a half rotation of the first ring member about the common axis.

In preferred embodiments the first engagement means is connected to, or integral with, the first ring member. This allows for a reduction in the number of components that are movable relative to one another. For practical purposes, however, the first engagement means and first ring member could be manufactured separately and then assembled. Preferably the first engagement means comprises an arm. Particularly preferably the first engagement means comprises an arm having a slot and a contact end member, and in especially preferred embodiments two, three or four arms (e.g. four arms) each having a slot and a contact end member are provided. The contact end is preferably an upwardly extending component that contacts (e.g. rides over) the deflector.

Preferably the second engagement means is connected to, or integral with, the second ring member. In preferred embodiments the second engagement means comprises a plurality of protrusions. The protrusions are preferably equally spaced apart. Preferably the protrusions extend in an arc approximately between a quarter way and half way around the common axis.

In preferred embodiments, when the arm is moved radially outwardly the slot (e.g. the end of the slot) of the arm engages with one of the plurality of protrusions. In such an arrangement the rotation of the first ring therefore pulls the second ring member along (i.e. causes it also to rotate). However, by using an alternative (but equally suitable) coupling mechanism it is also possible for the first ring member to push the second ring member along.

In preferred embodiments, the counter also comprises a third ring member being coaxially arranged about the common axis of the first and second ring members. Also, the deflector is preferably connected to, or integral with the third ring member. Preferably the third ring member is fixed in use to prevent rotation of the third ring member. Preferably, the third ring member also comprises a limiting mechanism to limit free rotation of the second ring member relative to the third ring member about the common axis. This prevents over-rotation of the second ring member, which would indicate an incorrect number of remaining doses.

Preferably, the limiting mechanism comprises a resiliently deformable portion for applying pressure on the second ring member for limiting the free rotation of the second ring member.

In this embodiment, the second ring member preferably comprises a plurality of substantially equally-spaced protrusions protruding from an upper circumferential edge of the second ring member, and the limiting mechanism engages with the protrusions for limiting the free rotation of the second ring member.

Furthermore, the third ring member preferably comprises one or more locating recesses disposed in an upper circumferential surface for engaging with correspondingly-shaped protrusions in a housing or container for preventing free rotation of the third ring member.

The first and second indicia can comprise one or more of: numbers, colours, letters and symbols. In preferred embodiments the first indicia comprise a first row of numbers, and said second indicia comprise a second and a third row of numbers. For example, the first row of numbers can represent units digits, the second row can represent tens digits, and the third row can represent hundreds digits.

Preferably the first row of numbers comprises repeated sets of integers, for example four sets of the numbers '0' to '9' (one set per quarter of the first ring member). Preferably the second row of numbers also comprises repeated sets of integers, for example two sets of the numbers '0' to '9' (the two sets filling half the second ring member). Preferably the third row of numbers comprises a set of integers (e.g. ten '1's and one '2' or ten '1's). Optionally the third row additionally includes blanks. This allows counting from '200' or '199' down to '0' respectively.

The first and second indicia can be printed, cut out from, embossed, moulded, adhered, incorporated, painted and/or otherwise marked (e.g. laser marked) on the first and second ring members.

In preferred embodiments, the second ring member comprises a display cover element for obscuring a view of the first indicia. This enables the counter to indicate that the number of doses has reached zero and requires replacing.

In preferred embodiments at least part of the drive mechanism is integral with the first ring member. Preferably the drive mechanism comprises a pawl-and-teeth mechanism comprising two pawls. Broadly speaking the drive mechanism translates vertical movements, e.g. of a junction member or medicament container, into rotational movements, e.g. of the first ring member.

Preferably the counter is attached to a dispenser having a body for receiving a medicament container and a dispensing mechanism for dispensing a dose of medicament from the container. For example, the rotating of the first ring member can be performed in response to the dispenser being actuated. Thus, the count can be indicative of doses of medicament dispensed from, or remaining in, the container.

In preferred embodiments the dispenser includes a housing having a window to allow only a portion of the first and second indicia to be displayed. The window may be a hole in the housing or may be a transparent area of the housing. This allows a precise reading of the quantity of unit product, such as metered doses of medicament, remaining in the container or dispensed therefrom.

In a related aspect of the invention there is provided a dispenser comprising the counter as hereinbefore described.

In another related aspect of the invention there is provided a dispenser comprising: a body for receiving a medicament container; a medicament container; a dispensing mechanism for dispensing a dose of medicament from said container; and a counter as hereinbefore described. Preferably the dispenser is a pressurised metered-dose inhaler (pMDI).

In yet another related aspect of the invention there is provided a counter strip comprising a row of numbers, said numbers comprising repeated sets of integers.

In yet another related aspect of the invention there is provided a counter strip comprising a first and second row of numbers, wherein said first row comprises repeated sets of integers and said second row comprises a set of integers.

BRIEF DESCRIPTION OF THE DRAWINGS

These and other aspects of the invention will now be further described, by way of example only, with reference to the accompanying figures in which:

FIGS. 7a and 7b show a preferred drive mechanism for a counter according to the present invention;

DETAILED DESCRIPTION OF PREFERRED EMBODIMENTS

Dispenser

To explain the invention, a brief overview of some features and operating principles of exemplary dispensers is initially provided. As used herein the term "dispenser" is intended to mean any device having a body suitable to receive a container holding a product and which has a mechanism to dispense the product from the container upon actuation.

Figure 1:
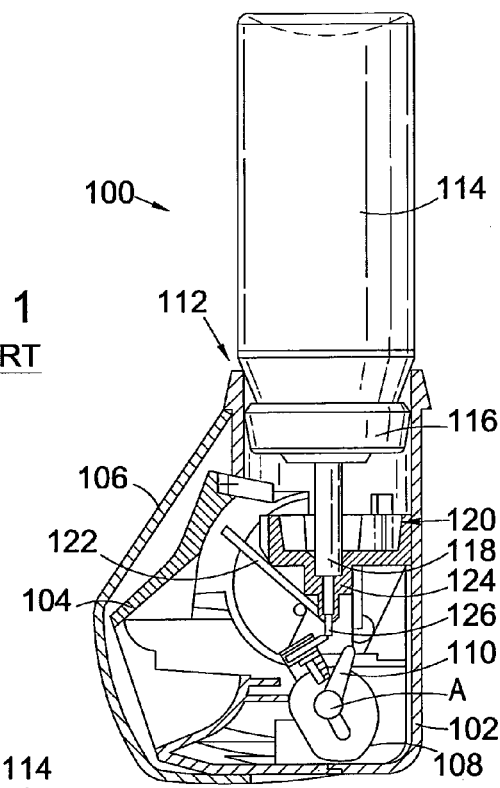
FIG. 1 is a cross-sectional view of a dispenser to which a counter according to the present invention may be attached.

FIG. 1 shows in partial cross section an example of a breath-actuated, kink valve dispenser. The dispenser 100 comprises a body 102 with a mouthpiece 104 and a pivotable mouthpiece cover 106. The mouthpiece cover is pivotable about an axis, A, low in the body and carried on a cam arrangement comprising two cam lobes (only one cam lobe 108 is shown), together with a central finger 110. The body has an opening 112 for receiving a medicament container 114. The container may be held fixedly in place at the upper end of the body, at a location where the body extends completely around a metering valve assembly of the container (not shown). The metering valve assembly comprises a metering chamber 116 and an outlet stem 118. Alternatively, or additionally, if the container is housed entirely within the dispenser, the container may be held at an end distal of its metering valve assembly, for example by a cap portion of an outer housing.

Moulded inside the body, inwards of the opening 112 are internal grooves (not shown). A junction member 120 is slidably accommodated in the body with the grooves engaged by ribs in its periphery. The junction member has a pair of pivot clips (not shown) for pivotally locating the flap 122 in the junction member 120. Centrally, the junction member has a socket 124 for the outlet stem 118 of the metering valve assembly. The socket is continued by a passage 126, which has a thin wall, kinkable portion and a nozzle end. The nozzle end is in a movable part of the junction member. The main part and the movable part of the junction member are connected by a living hinge.

The moving part of the junction member 120 also carries a pair of sears (not shown) that are arranged to engage with latches on the underside of flap 122 as described below. The movable part of the junction member also carries a finger for engagement with the cam arrangement.

Initially when the dispenser is closed the flap is unlatched and the movable part of the junction member is in its lower position. The kinkable portion, sometimes called a kinkable valve, is open. On opening of the mouthpiece cover 106, the central finger of the cam arrangement acts on the movable part of the junction member to close the kink valve. The movement of the movable part of the junction member also serves to engage the sears of the movable member with the latches of the flap, thereby fixing the flap in an upper position. The junction member 120 is also lifted by the main cam lobes 108 against an internal spring (not shown) of the metering valve assembly, with displacement of the stem 118 inwards of the container. Further lifting of the mouthpiece cover 106 opens the container valve and a metered dose is released into the upper part of the tube, the dose being retained by the closed kink valve acting as a closed valve.

Breathing in through the mouthpiece causes an air flow through the dispenser and impinges on flap 122. This causes release of the sears and the kink tube tends to straighten under the action of its own resilience and the pressure of the retained dose. The dose is thus released through the nozzle into the mouthpiece for inhalation. The flap may also carry a finger (not shown) that can act on the moveable part of the junction member to ensure that the kink valve is opened when the flap is breath actuated.

These and other features of exemplary dispensers are described in more detail in Clinical Designs Limited's prior PCT applications WO 1998/41254 (U.S. Pat. No. 6,422,234); WO 2002/11802 (U.S. Pat. No. 7,036,505); WO 2002/058772 (U.S. Pat. No. 6,866,038) and especially WO 2004/073776 (US 2007 062522), the disclosures of all of which are fully incorporated herein by reference.

Tolerance Adjustment Mechanism

Due to the build up of manufacturing tolerances in the manufacture of the dispenser and medicament container, the medicament container may be insufficiently accurately located longitudinally with respect to the dispenser body and the cam mechanism. This may result in an insufficient dose being metered from the container.

In preferred dispensers for use with the counter of the present invention, the dispenser comprises a tolerance adjustment mechanism such as the can fixture mechanism described in WO 03/080161 (also U.S. application Ser. No. 10/508,688).

In the preferred dispenser, the correct relative locations of the container and the body 102 are achieved during assembly of the dispenser. A pre-assembled body 102, mouthpiece cover 106, junction member 120 and release member, or flap 122 are set to their mouthpiece cover 'open' position (i.e. with the cover pivoted down from the FIG. 1 position). In this position, the junction member 120 is lifted, which would ordinarily displace the stem 118 of an installed container when installed. With the components set to their 'open' position, a container 114 is introduced into the tubular section of the body 112. With the container 114 and body 112 properly aligned, the stem 118 engages in the socket 124 in the junction member 120. A predetermined force F is applied to ensure that the spout is fully depressed. This causes the container to release a dose of medicament into the kinkable valve. With the force still applied, the relative positions of the body 102 and container 114 are fixed (examples given below).

Once the relative positions of the container and body are fixed, the release mechanism may be triggered to release the dose of medicament metered during the above process and the mouthpiece cover moved to the closed position (as shown in FIG. 1), after which the dispenser is ready for shipment.

For fixing the relative positions of the container and body, a printed label coated with self-adhesive may be wrapped around the joint between the body and the container (either all of the way around the joint, or partially).

Alternatively, instead of a self-adhesive label, a shrink-wrap label all of the way around the joint may be used. This is particularly advantageous where the body stands slightly proud of the container.

Alternatively, instead of labels, the container and body may be welded together to fix their positions relative to one another. For example, when the container is an aluminium or glass extrusion with a coating of polypropylene of sufficient thickness, a ultrasonic welding process may be used to weld the coated portion to the body.

Alternatively, the container and body may be glued together in the correct relative positions using a low temperature hot melt adhesive or fast curing two-part adhesive.

Of course, the skilled reader would appreciate that there are a many number of alternative fixing means available for the purpose of fixing the relative positions of the container and body.

In an alternative tolerance adjustment mechanism, an abutment feature is used as described in WO2007/029019 (also U.S. application Ser. No. 11/991,680).

In this alternative mechanism, the dispenser is provided with a closed sleeve or housing, much like the housing 1402 shown in FIG. 14. This housing provides abutment for the exposed end of the container 114. An adjustable abutment is provided between the container 114 and the housing. The required size of the adjustable abutment is calculated by measuring the distance between the exposed end of the container 114 and the opening 112 of the body 102 to give the measured 'source' length. With knowledge of the effective length of the source, and knowledge of the distance below the opening 112 at which the outlet stem 118 should be located, one can calculate the required size of adjustable abutment taking into account the length of the housing.

After sizing the abutment, the housing is assembled to the body 102 and the housing is laser welded to the body. The result is that the source is supported firmly for displacement of the outlet stem 118 inwards on operations of the cam mechanism by opening of the mouthpiece cover.

The abutment is made, for example, of an aluminium honeycomb of a wall thickness that can be readily compressed to the required dimension, yet can resist the force exerted on it in operation, i.e. when the container is urged against it. It should be noted that the compression is plastic and permanent. The abutment may be fixed to the housing, for example by welding.

Alternatively, the abutment may form part of the housing, and the abutment may comprise many thin, radial ribs protruding from the closed end of the housing and arranged around the radially outer part of that closed end. The ribs are plastically deformable. They can be compressed and form an abutment.

Drive Mechanism

The term "drive mechanism" is to be interpreted broadly as any means by which the dispensing of a dose from the medicament container is linked to a count being made by the counter. In described embodiments the dispensing of a dose will involve a vertical movement, e.g. of junction member 120, as described earlier with reference to FIG. 1. In the described preferred embodiment, this vertical movement is translated into an incremental rotation that is counted. In other embodiments the vertical movement that is translated into an incremental rotation may be the movement of a medicament container.

Figure 2:
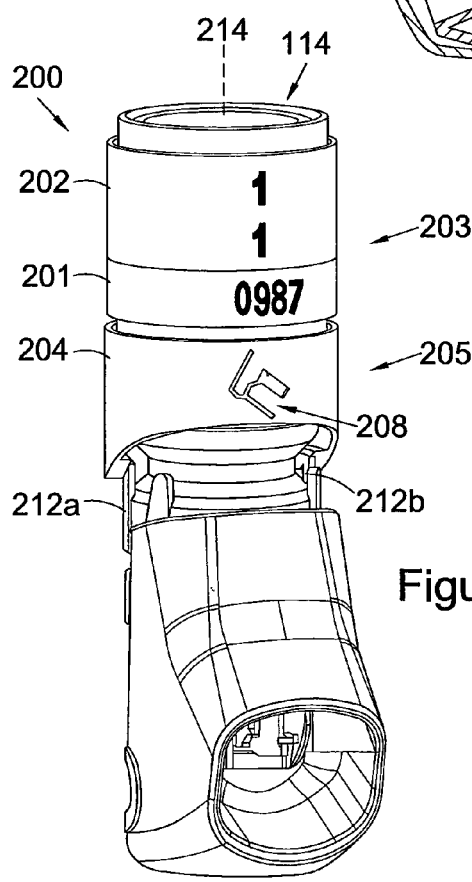
FIG. 2 is a perspective view of a dispenser including a counter according to the present invention.
Figure 3:
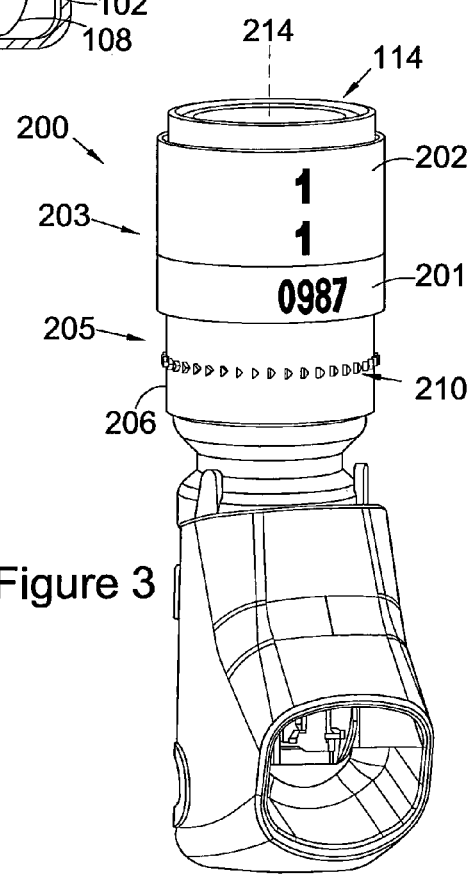
FIG. 3 is a perspective view of a dispenser including a counter according to the present invention.

FIGS. 2 and 3 schematically show a dispenser 200 having a counter 203 and a drive mechanism 205. The counter comprises a first ring member 201 and a second ring member 202. The drive mechanism 205 is a pawl-and-teeth mechanism having a pawl-bearing member 204 (not shown in FIG. 3) and a teeth-bearing member 206 (partially hidden from view in FIG. 2). In this particular embodiment, the teeth-bearing member 206 is a hollow cylinder integral with the first ring member 201. The pawl-bearing member extends fully around the teeth-bearing member 206. The reverse configuration may also be used, i.e. the pawl bearing member 206 may be integral with the first ring member 201. This arrangement is shown in FIG. 7.

Two pawls 208 are defined by a cutaway portion of pawl-bearing member 204. The pawls operatively engage with a ring of teeth 210 moulded on an outwardly facing surface of the teeth-bearing member 206 by means of inwardly extending protrusions on the tips of the pawls, as will be described in more detail later. A pair of arms 212a, 212b extend downwardly from the pawl-bearing member on either side of the metering valve assembly. The arms can be spring-loaded against, or affixed to, an upper portion of a junction member (hidden from view). The junction member moves vertically when a dose is dispensed. Alternatively the arms can be spring-loaded against, or affixed to, a moving container, e.g. a moving medicament container.

The action of lifting the junction member 120 (which causes the release of a dose from a pressurised medicament container 114) imparts an upward force on the pawl-bearing member 204 in a direction parallel to the vertical axis 214 of the dispenser 200. This results in frictional engagement between the pawl(s) and the teeth. In turn, the teeth-bearing member 206 and first ring member 201 are rotated (clockwise in this particular case) about the vertical axis 214 by an increment.

Once a dose is released and the mouthpiece cover is being closed or is closed, the junction and pawl-bearing members are able to move downwards to their original positions by, for example, an internal spring (not shown) of the medicament container 114. This downward movement also results in frictional engagement between the pawl-bearing and teeth-bearing members, resulting in a further clockwise rotation of members 206, 201 about the vertical axis 214 by an increment.

Taken together, these two increments of rotation define a "complete" incremental rotation of the first ring-like member 201 from a first to a second position.

Figure 4A:
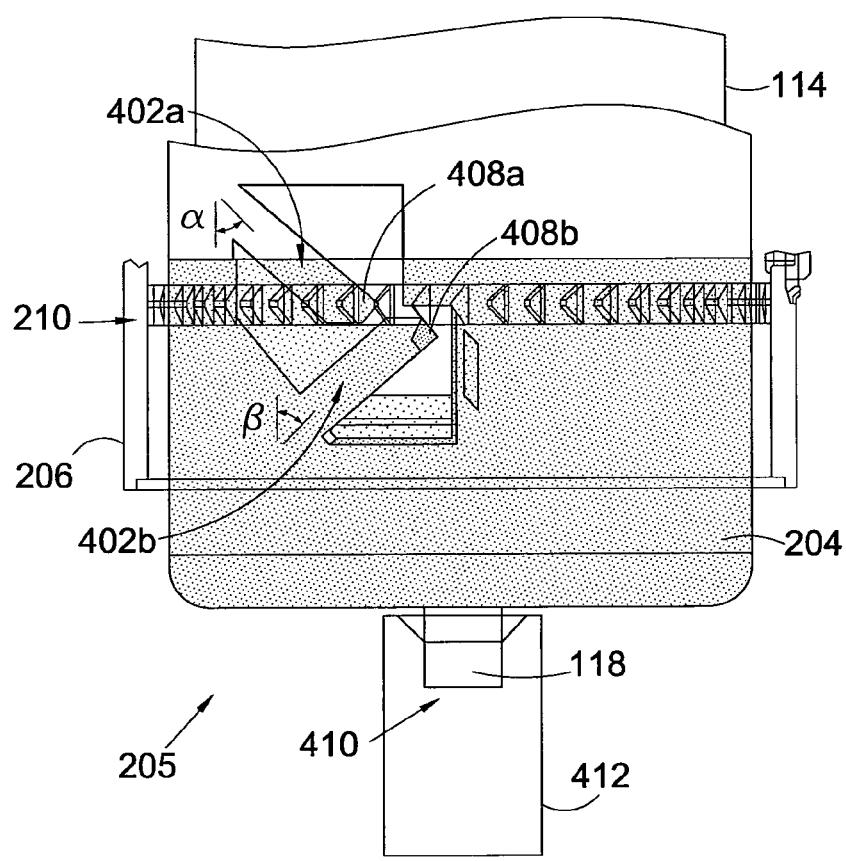
FIGS. 4a and 4b show a drive mechanism for a counter according to the present invention.

FIG. 4a illustrates an exemplary drive mechanism 205 in which the ring of teeth 210 is disposed on an inwardly facing surface of the teeth-bearing member 206, with the pawl-bearing member 204 being disposed within its bore. It will be recognised that the pawl- and teeth-bearing members are in a reverse configuration compared to the configuration shown in FIGS. 2 and 3, though the operating principle of the drive mechanism remains substantially the same.

Two pawls 402a, 402b, are integrally defined in the pawl-bearing member 204, by a cutaway portion of its body. Viewed from this perspective, each pawl extends toward the ring of teeth 210 in an annular plane of the pawl-bearing member 204, at about the same (but opposite) angle α, β. The second (lower) pawl 402b is offset in a circumferential direction relative to the first (upper) pawl 402a. The pawls each have a root end and a free end. A lip 408a, 408b, protrudes radially outwardly from each of the free ends, to operatively engage with the teeth.

The valve stem 118 of the metering valve assembly inserts down through the clearance hole in the base of the pawl-bearing member 204 to rest on a shelf 410 in a stem block 412. This differs from the preferred configuration shown in FIGS. 2 and 3. It will be appreciated that this difference, in itself, is not of particular significance in the context of the drive mechanism.

In operation, and viewed from this perspective, the pawl-bearing member 204 moves up and down, and rotates, relative to the teeth-bearing member 206. For convenience, the upward and downward movements of the pawl-bearing member 204 will be referred to as the 'count stroke' and 'return stroke', respectively. These terms are only used for convenience and are not to be construed as meaning that a count only occurs during the count stroke. It will be apparent to those skilled in the art (and from the following description) that a count may occur during the count stroke, return stroke or a combination of both strokes.

Figure 5A:
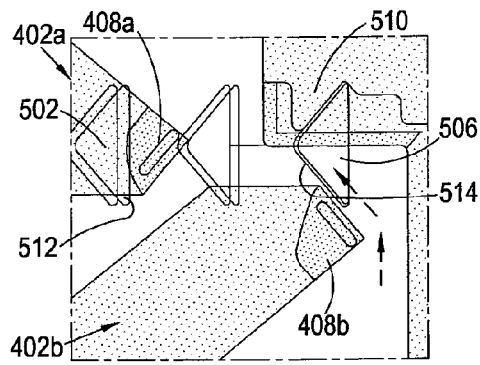
FIGS. 5a to 5d are schematic diagrams showing a part of the principle of operation of the drive mechanism of a counter according to the present invention.
Figure 5B:
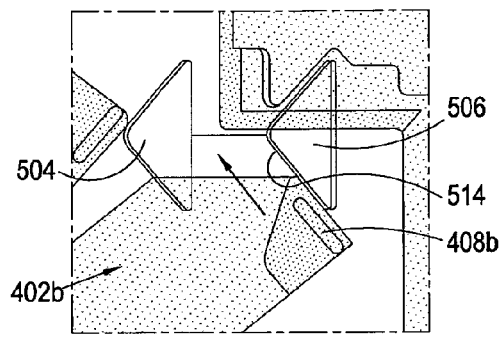
Figure 5C:
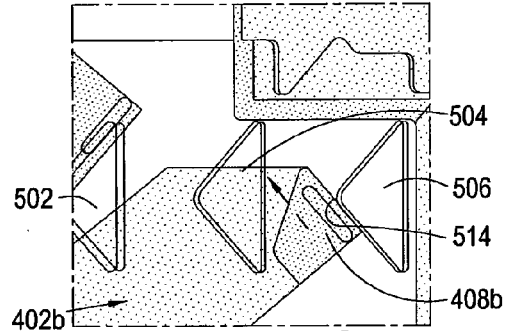
Figure 5D:
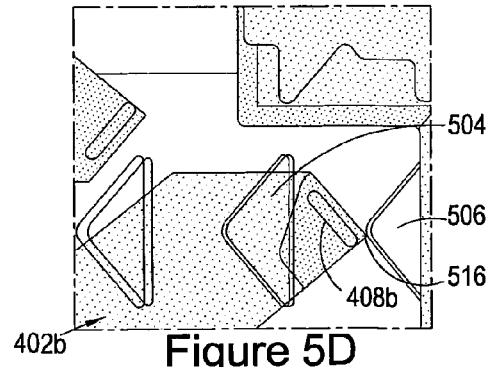

FIGS. 5a to 5d show a sequence of cross-sectional views of the drive mechanism during the count stroke. In FIG. 5a, the pawl-bearing member is at rest on the teeth by means of a protruding block 510. An upwardly directed force on the pawl-bearing member initially results in frictional engagement between the lip 408a of the first (upper) pawl 402a and a vertical face 512 of tooth 502. This action guides the pawl-bearing member substantially vertically upwards, until such a time as the lip 408b of the second (lower) pawl 402b engages with a lower, sloped face 514 of tooth 506 (FIG. 5b). This effects an upward diagonal movement, which proceeds until lip 408b reaches, and then surpasses, the apex 516 of tooth 506 (FIGS. 5c and 5d, respectively). At the same time, the first (upper) pawl 402a flexes slightly inwardly to allow lip 408a to pass over tooth 502 (FIG. 5c). Dashed arrows indicate the direction of movement.

FIGS. 6a to 6d show a sequence of cross-sectional views of the drive mechanism during the return stroke. Like elements to those of FIG. 5 are indicated by like reference numerals.

Figure 6A:
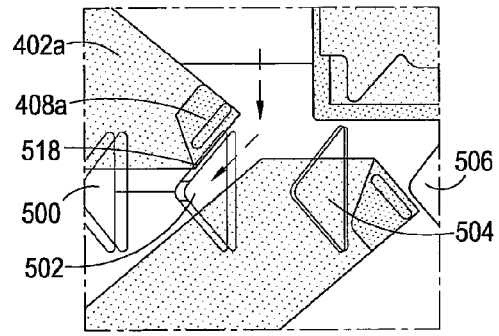
FIGS. 6a to 6d are schematic diagrams showing another part of the principle of operation of the drive mechanism of a counter according to the present invention.
Figure 6B:
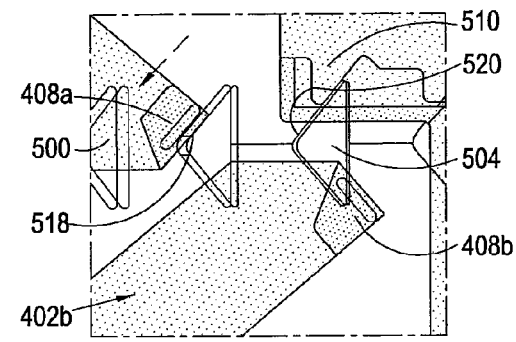
Figure 6C:
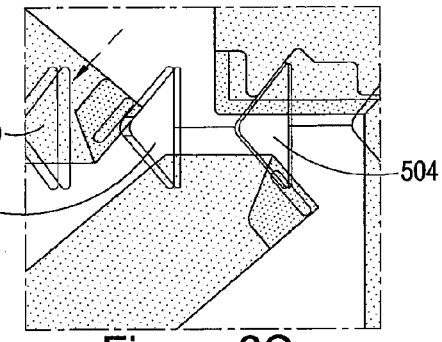
Figure 6D:
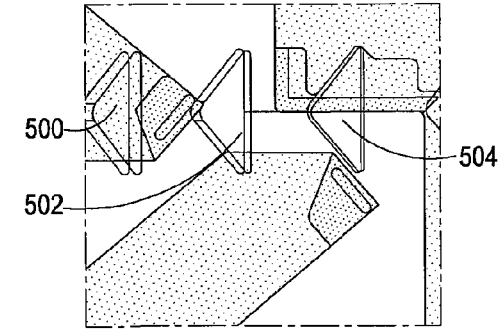

In FIG. 6a, which corresponds substantially to FIG. 5d, the lip 408a of the first (upper) pawl 402a moves vertically downwards until it frictionally engages with an upper, sloped face 518 of tooth 502, resulting in a downward diagonal movement. In FIG. 6b, the lip 408a has proceeded further down face 518, and block 510 now engages an upper, sloped face 520 of tooth 504. This time the second (lower) pawl 402b flexes slightly inwardly to allow lip 408b to pass over tooth 504. This proceeds until the pawl-bearing member again comes to rest on the teeth (FIGS. 6c and 6d). FIG. 6d corresponds substantially to FIG. 5a, but rotated by one tooth, i.e. from tooth 506 to tooth 504.

Figure 4B:
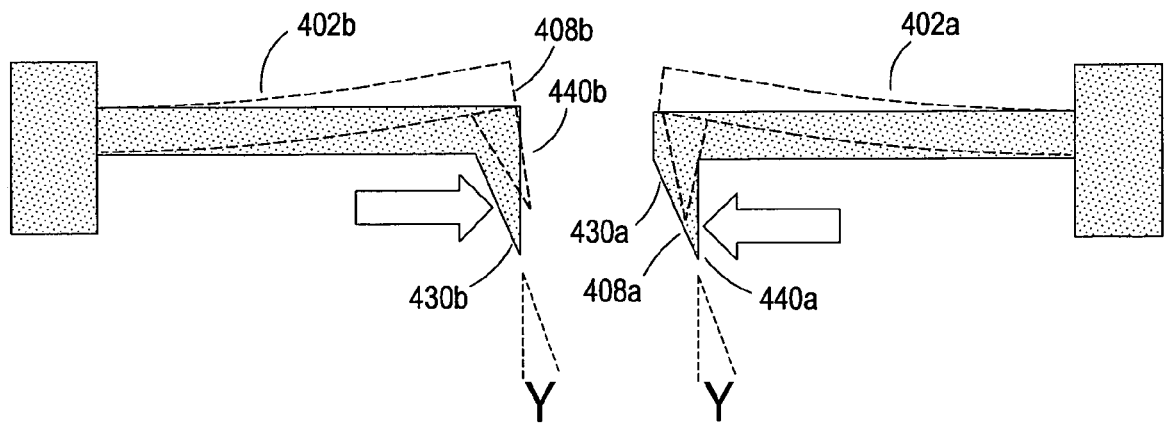

Referring to FIG. 4b, this shows a side profile of the pawls 402a and 402b and the lips 408a and 408b. Each lip comprises a driving engagement face 440, which contacts a tooth during a driving engagement of that lip 408. Each lip also comprises a sliding engagement face 430, which enables a lip 408 to contact and lift over a tooth without engaging the tooth. The large arrows denote the faces of the pawl lips that contact teeth during one of the strokes. The opposite faces (shown without arrows) contact teeth during the other stroke. The angle γ (that is the angle of the slope of the sliding engagement face 430 of the lip with respect to a vertical axis in the figure) must be sufficiently large enough to enable the lip 408b lift away and ride over the teeth when lip 408a is engaged with a tooth (i.e. driving engagement face 440a is in contact with, and drivingly engaged with a tooth). An angle greater than 15° is preferred. If the angle is less than 15°, the pawl may not lift above the tooth.

FIG. 7a illustrates a preferred embodiment of the drive mechanism 205 in which the ring of teeth 210 is disposed on an outwardly facing surface of a teeth-bearing member 206, which is placed within the bore of the pawl-bearing member 204.

Two pawls 402a, 402b, are integrally defined in the pawl-bearing member 204, by a cutaway portion of its body. Viewed from this perspective, each pawl comprises two arms extending toward the ring of teeth 210 in an annular plane of the pawl-bearing member 204. The second pawl 402b is offset in a circumferential direction relative to the first pawl 402a. A lip 408a, 408b, protrudes radially outwardly from the point at which the two arms meet, to operatively engage with the teeth.

FIG. 7b shows a side profile of the pawls 402a, 402b. The numerals of FIG. 4b refer to like features of FIG. 7b. As with FIG. 4b, the angle γ (i.e. the angle of the sliding engagement face 430 from the vertical of the drawing) must be sufficiently large enough to enable the sliding engaging face 430 to lift up and ride over the tooth (not shown). For example, the angle is preferably larger than 15°. More preferably, the angle is approximately 45°. It will also be noted that the orientation of the first pawl 402a is reversed to that shown in FIG. 4b. It will be appreciated that the engaged pawl (i.e. the pawl in driving engagement with the tooth) experiences a compression force that forces the pawl towards the toothed surface during engagement.

In operation, and viewed from this perspective, the teeth-bearing member 206 moves up and down (driven by the actuation of the junction member as described above), causing the pawl-bearing member 204 to rotate relative to the teeth-bearing member 206. For convenience, the upward and downward movements of the teeth-bearing member 206 will be referred to as the 'count stroke' and 'return stroke', respectively.

Figure 8A:
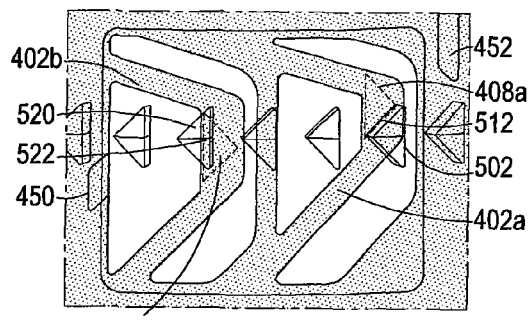
FIGS. 8a to 8d are schematic diagrams showing a part of the principle of operation of the preferred drive mechanism of a counter according to the present invention.

FIGS. 8a to 8d show a sequence of cross-sectional views of the preferred drive mechanism during the count stroke. In FIG. 8a, the teeth- and pawl-bearing members are at rest. An anti-slip bar 450, comprising a protrusion extending from the inner surface of the pawl-bearing member, is in an engaged position that is in line with the teeth to prevent non-count rotation of the pawl-bearing member (i.e. rotation of the pawl-bearing member in an opposite direction to that of the pawl-bearing member during a count). The anti-slip bar 450 is configured to prevent relative rotation between the teeth-bearing member and pawl-bearing member in a non-count direction by blocking motion of the pawl-bearing member. The bar extends sufficiently from the inner surface of the pawl-bearing to hit one of the teeth, but not the outer surface of the teeth-bearing member.

An upwardly directed force on the teeth-bearing member initially results in an edge of the lip 408a coming into frictional engagement with a sloped face 512 of tooth 502 and moves the anti-slip bar 450 out of the path of the teeth to permit rotation. Further upward movement of the teeth-bearing member causes rotational movement of the pawl-bearing member (towards the left of the figure). At the same time, the inner non-vertical surface of lip 408b (shown as the arrowed surface in FIG. 7b) contacts a vertical non-leading edge 522 of tooth 520, which causes the pawl 402b to lift away from the plane of the teeth, and permits the pawl 402b to ride over the tooth without engagement.

Rotational movement of the pawl-bearing member continues until lip 408a and surface 512 no longer contact. At this point, lip 408b has cleared tooth 520, and falls back to the plane of the teeth by virtue of the pawl arms being resiliently deformable. Further upward motion of the teeth-bearing member has no further effect on rotation of the pawl-bearing member. However, a second anti-slip bar 452 (configured similarly to anti-slip bar 450) is brought into the path of the teeth to prevent backward (i.e. non-count) rotation of the pawl-bearing member.

FIGS. 9a to 9d show a sequence of cross-sectional views of the drive mechanism during the return stroke. Like elements to those of FIG. 8 are indicated by like reference numerals.

Figure 9A:
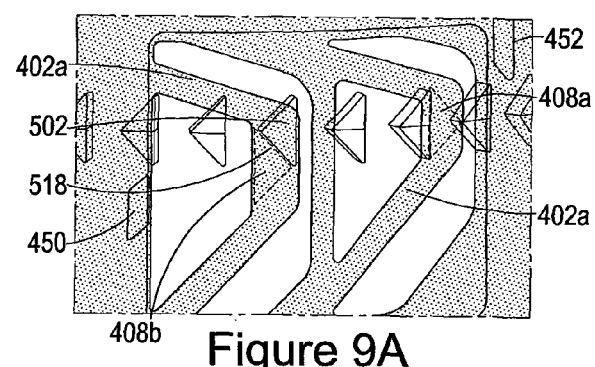
FIGS. 9a to 9d are schematic diagrams showing a part of the principle of operation of the preferred drive mechanism of a counter according to the present invention.
Figure 8B:
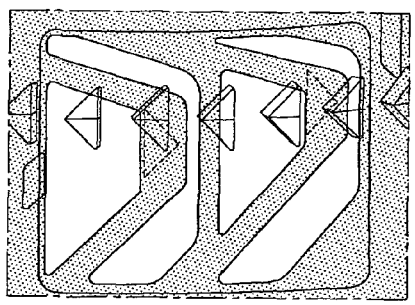
Figure 9B:
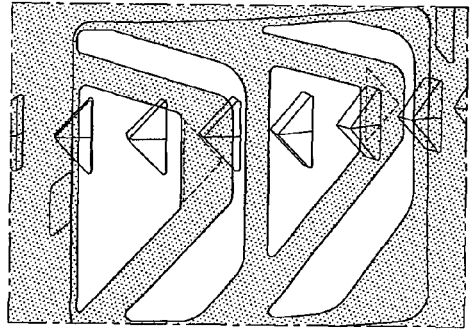
Figure 8C:
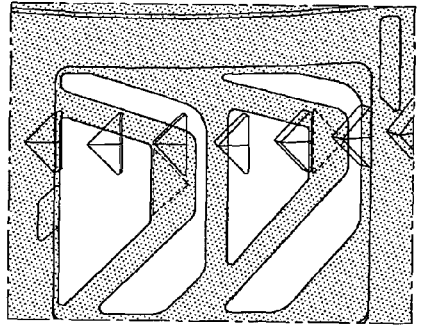
Figure 9C:
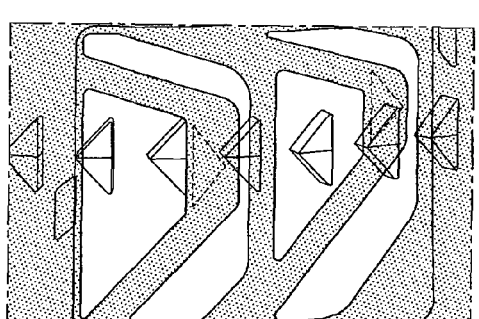
Figure 8D:
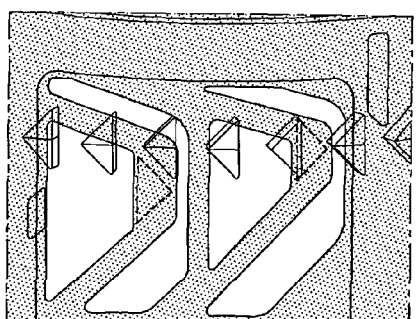
Figure 9D:
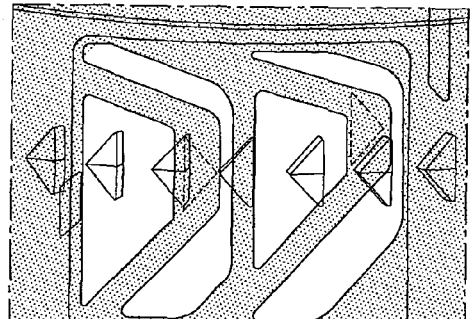

In FIG. 9a, which substantially follows FIG. 8d, the teeth-bearing member is lowered until lip 408b of the first pawl 402b frictionally engages with a lower, sloped face 518 of tooth 502 (simultaneously, the second anti-slip bar 452 is moved from the path of the teeth). Further downward movement of the teeth-bearing member causes rotational movement of the pawl-bearing member by virtue of the face 518 and lip 408a being frictionally engaged.

Face 518 proceeds further down lip 408b. At the same time, the inner non-vertical surface of lip 408a contacts a vertical non-leading edge of a tooth, which causes the pawl 402a to lift away from the plane of the teeth, and permits the pawl 402a to ride over the tooth without engagement.

Rotational movement of the pawl-bearing member continues until lip 408b and surface 518 no longer contact. At this point, lip 408a has cleared the tooth over which it was riding, and falls back to the plane of the teeth by virtue of the pawl arms being resiliently deformable. Further downward motion of the teeth-bearing member has no further effect on rotation of the pawl-bearing member. However, the first anti-slip bar 450 is brought back into the path of the teeth to prevent backward rotation of the pawl-bearing member.

Although the foregoing discussion describes the case where the pawl-bearing member rotates about an axis (i.e. rotates relative to the dispenser as a whole), it is equally possible that the teeth-bearing member rotates. Naturally it is also possible that the teeth could point in either direction around the circumference of the teeth bearing member.

It will be appreciated that a rotational displacement need not be performed by way of two engagements (though this may be beneficial), nor need it comprise vertical and rotational movement. For example, a drive mechanism providing purely rotational motion, in other words without vertical movement, could also be used.

Counter

FIGS. 10 to 19 provide various depictions of the counter in more detail.

Figure 10:
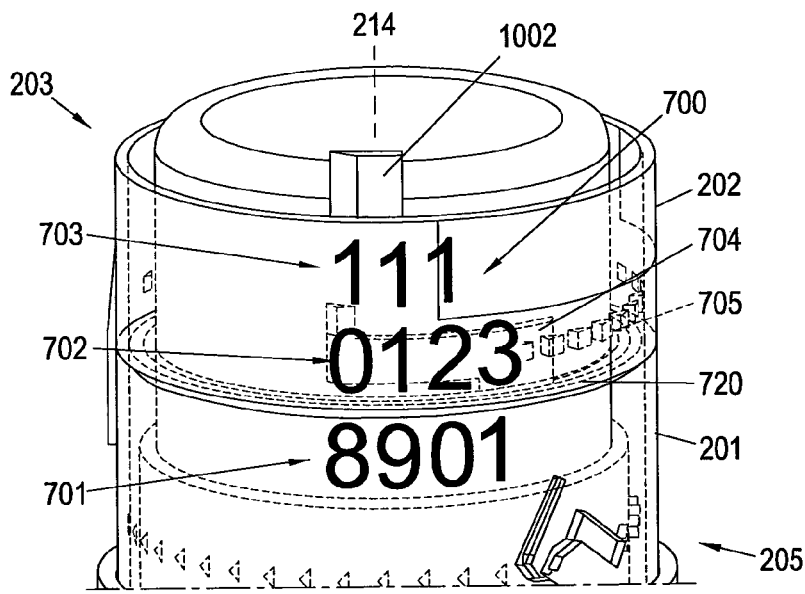
FIG. 10 is a perspective view of a counter according to the present invention.

Turning first to FIG. 10, the counter 203 is comprised of first ring member 201 and second ring member 202. The ring members are rotatably and coaxially arranged about the central axis 214, encircling the container of the dispenser. The second ring member is arranged substantially flush on top of the first ring member, with their outer circumferential surfaces being aligned so as to form a substantially continuous surface interrupted only by a hairline 720 where the two ring members meet. A pawl-bearing member 205 of a drive mechanism is integral with the first ring member 201.

A first row of numbers 701 ('8', '9', '0', '1') is displayed on the first ring member 201, with a second row of numbers 702 ('0', '1', '2', '3', '4') and a third row of numbers 703 ('1', '1', '1') displayed on the second ring member 202. For clarity, only some of the numbers are depicted. A coupling mechanism 700 comprising an arm 704, a series of equally spaced protrusions 705, and a deflector 1002 can also be seen. The coupling mechanism allows the first ring member 201 to be coupled to the second ring member 202, so that they can be rotated in tandem by the drive mechanism when coupled, as detailed below. The spaced apart protrusions 705 are formed on an inner surface of the second ring member 202, and in this particular case extend only half way around the axis.

It will become clear in due course that, depending on the counting scheme used, multiple arms and/or deflectors may be provided. However, for purposes of clarity only, only one arm and/or deflector is depicted in these figures.

Figure 11:
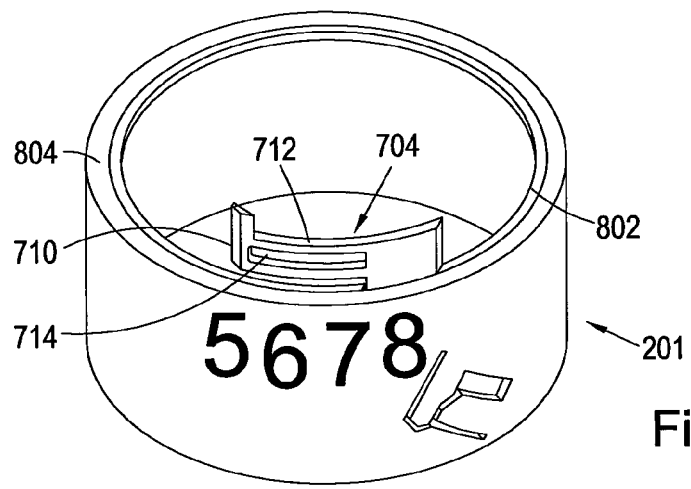
FIG. 11 is a perspective view of a first ring member of the counter of FIG. 10.

Referring now to FIG. 11, the arm 704 is integrally formed with an annular band 802 that fixedly sits in a recess of an upper radial surface 804 of the first ring member 201. Alternatively, the arm 704 can be directly mounted on, or integral with, upper radial surface 804. The arm 704 has a slotted body 712 which extends arcuately with approximately the same curvature of first ring member 201, and an upwardly extending contact end 710.

Figure 12:
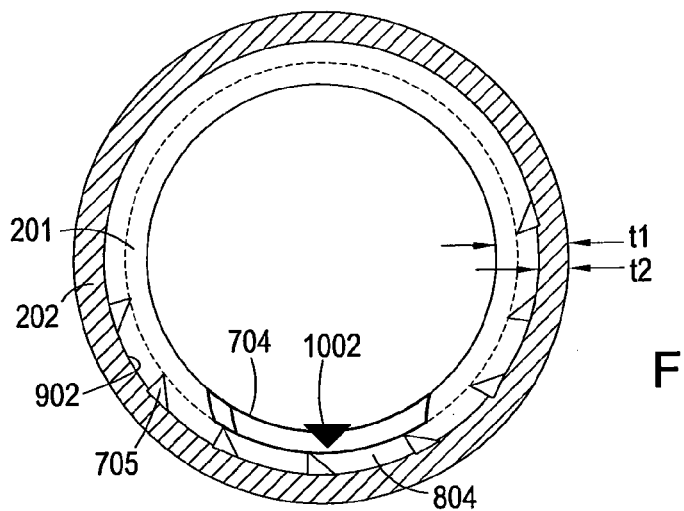
FIG. 12 is a top view of the counter of FIG. 10.

With reference to FIG. 12, being a view of FIG. 10 from above, the second ring member 202 (shown as a shaded ring) is slidably mounted on an outer portion of the upper radial surface 804 of the first ring member (shown as a blank ring, part of which is hidden from view underneath the shaded ring). From this perspective, it is apparent that the thickness of the second ring member 202, designated 't2', is about a third of the thickness of the first ring member 201, designated 't1'. The thickness of the first ring member 201 may be consistent along its height or it may be tapered, it being thickest at its upper radial surface 804. The dashed line represents an imaginary boundary line between the arm 704 and the spaced apart protrusions 705 formed on the inner surface 902 of the second ring member 202.

FIGS. 13 and 14 show, in a series of corresponding perspective and downward views respectively, the operation of the coupling mechanism.

Figure 13A:
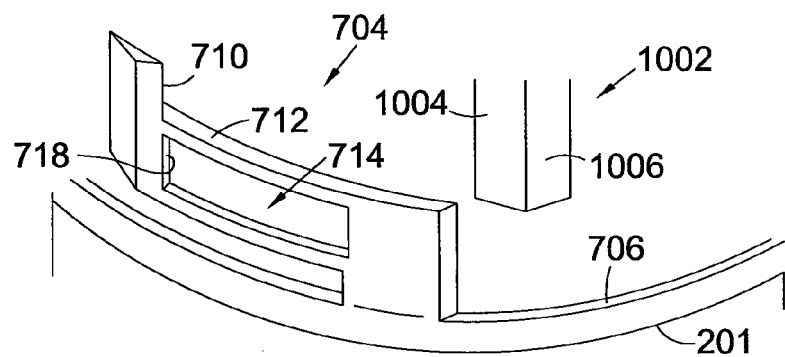
FIGS. 13a to 13d schematically show in perspective view the operating principle of a counter according to the present invention.
Figure 13B:
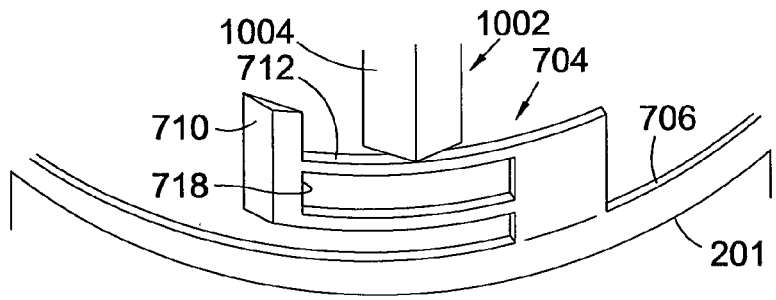
Figure 14A:
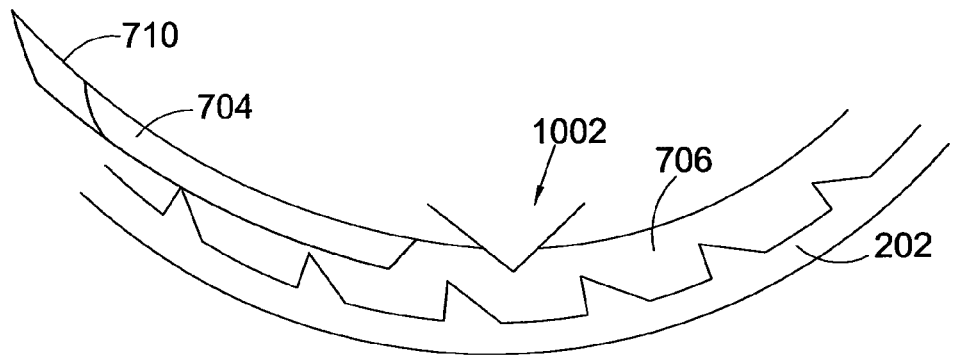
FIGS. 14a to 14d schematically show from a top view the operating principle of a counter according to the present invention.
Figure 14B:
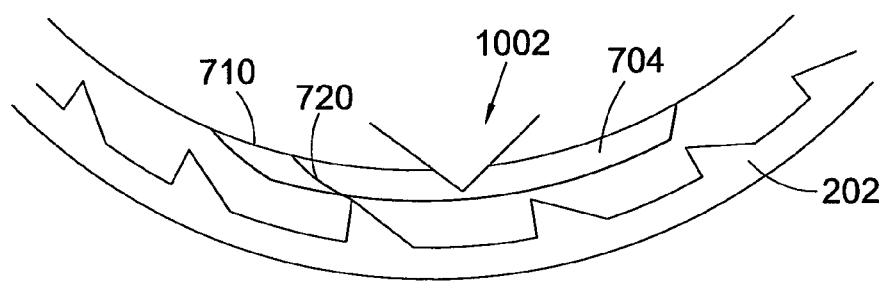

FIGS. 13a and 14a show the arm 704 at a distance from the deflector 1002. In FIGS. 13b and 14b, the first ring member 201 and arm 704 are rotated in an anticlockwise direction, so that the upwardly extending contact end 710 of the arm 704 approaches the deflector 1002. The deflector 1002 is fixed to the container, or alternatively to an upper portion of a housing of the dispenser and/or to a sleeve surrounding the container. The deflector extends downwardly only to such an extent that the body 712 of the arm is allowed to pass underneath unimpeded.

Figure 13C:
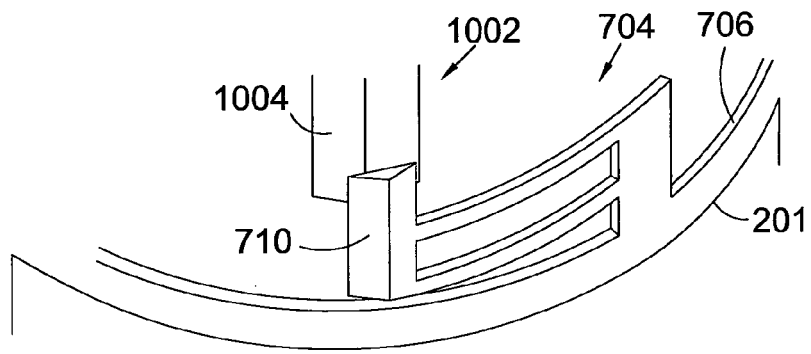
Figure 13D:
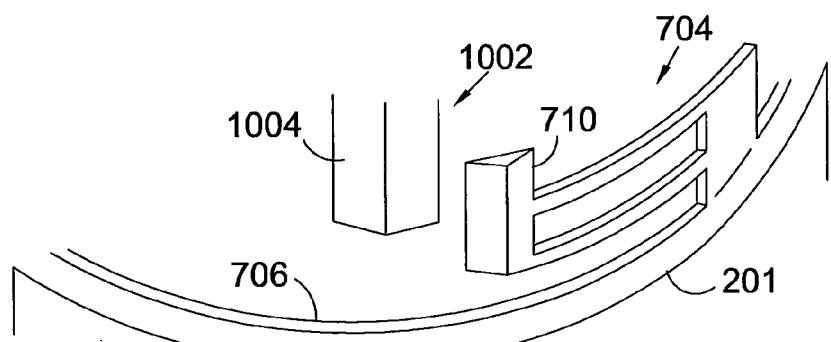
Figure 14C:
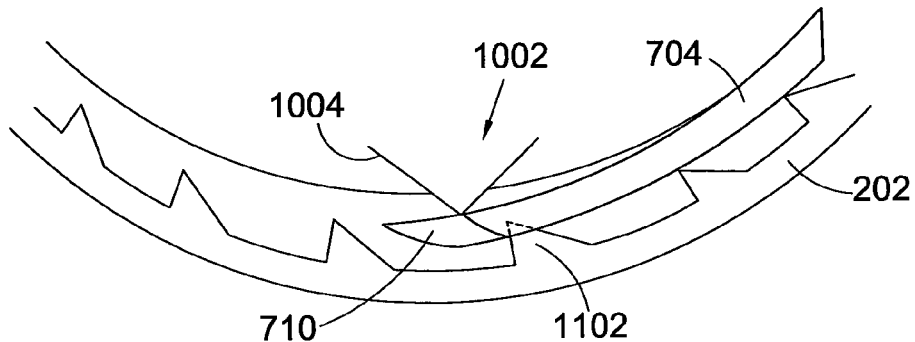
Figure 14D:
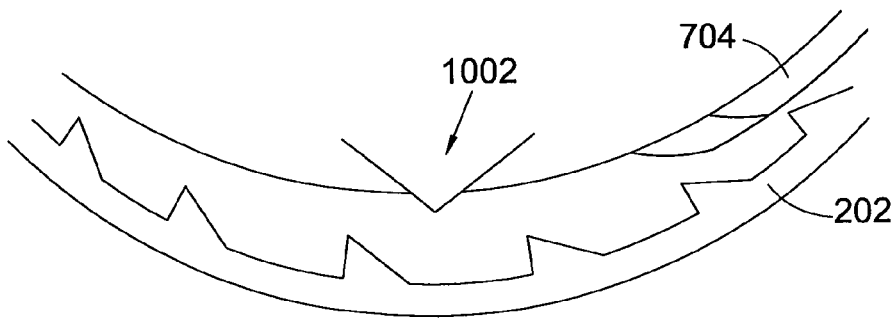

As the contact end 710 reaches an inclined face 1004 of the deflector 1002, the arm 704 is deflected outwards (FIGS. 13c and 14c). At this point a trailing end 718 of the slot 714 catches one of the teeth 1102, thereby causing the second ring member 202 to be pulled along. When the contact end descends down face 1006 of the deflector, the tooth 1102 is released by the trailing end of the slot and the arm returns to its non-flexed position (FIGS. 13d and 14d). As seen in FIG. 14b, the upwardly extending contact end 710 of the arm 704 may have a face 720 complementing the inclined face 1004 of the deflector 1002, to allow for a smooth deflection. Preferably the contact end 710 is pointed so that when it reaches the apex of deflector 1002, the arm can immediately begin to return to its non-flexed position.

As shown herein, the slot 714 forms an engaging portion of the arm 704, but it is recognized that any suitable engaging means could be used such as a hook. Accordingly, recesses could be formed in the second ring instead of protrusions.

The arm 704 is sufficiently flexible to permit a radially outward deflection (that is, towards the protrusions) when encouraged to do so, but also resilient enough to return to its original position. The counter may additionally comprise a second deflector that functions to move or deflect the engagement means (e.g. arm 704) back to its non-flexed position. This second deflector may, for example, be fixed to, or integral with, an inner surface of the second ring member 202. Additionally the second ring member is preferably slidably mounted on the first ring member so as to resist rotation when there is no engagement between the arm and the teeth.

Figure 15A:
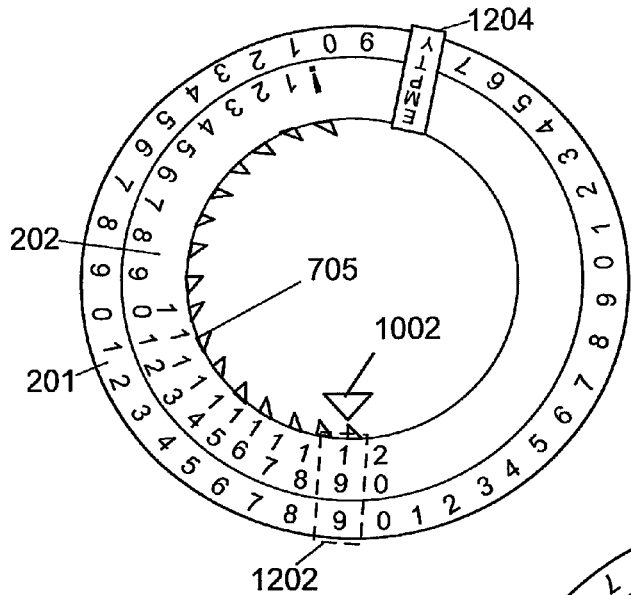
FIGS. 15a to 15c are schematic diagrams showing the principle of operation of a counter according to the present.

An exemplary counting scheme for a counter configured for 200 doses is now described with reference to FIGS. 15a to 15c, which show the first and second ring members in three different display positions. For convenience, the ring members 201, 202 are shown as flat rings. Also shown are the protrusions 705, the deflector 1002, a window 1202 through which the counter can viewed, and a display cover element 1204.

In this particular scheme, the first ring member 201 has a first row of numbers comprising four repeated sets of consecutive integers '0' to '9', i.e.:

0123456789012345678901234567890123456789.

Each set of integers covers a quarter turn of the first ring member 201, and here represents the 'units' digits of a count.

The second ring member 202 has second and a third rows of numbers. The second row comprises two repeated sets of consecutive integers '1' to '9' separated by a '0', while the third row comprises ten '1's optionally followed by a '2', e.g.:

11111111112
12345678901234567890

Similarly, each set of integers of the second and third rows covers a quarter turn of the second ring member 202. Here, the second row represents 'tens' digits, and the third row represent 'hundreds' digits of a count. Also shown on the second ring is a warning symbol in the form of an exclamation mark '!'.

In practice it may be more convenient to start a count at say '199' rather than '200', to avoid having to rotate the second ring member 202 initially. The integers forming the number '200' seen to the right of the window 1202 in FIG. 15a may therefore be omitted. Thus, when the first and second ring members are initially aligned in a housing of the dispenser, the first, second and third rows cooperatively display the number '199' (when read from top to bottom):

-----------------------------1111111111
--------------------0123456789012345678
012345678901234567890123456789012345678 where '-' indicates a blank space.

For each of the first nine dispensed doses, the first ring member is rotated anticlockwise by an increment, i.e. counting down from '9' to '0', until the number '190' is displayed. Then for the tenth dispensed dose, the first and second ring members are coupled by means of the coupling mechanism so that the ring members are rotated in tandem by an increment. This results in the number '189' being displayed through window 1202. For the subsequent nine dispensed doses, the first ring member is again rotated anticlockwise by increments until the number '180' is displayed. For the twentieth dispensed dose, the coupling mechanism is again engaged, so that the first and second ring members are rotated in tandem by an increment and the number '179' is displayed through the window 1202.

Figure 15B:
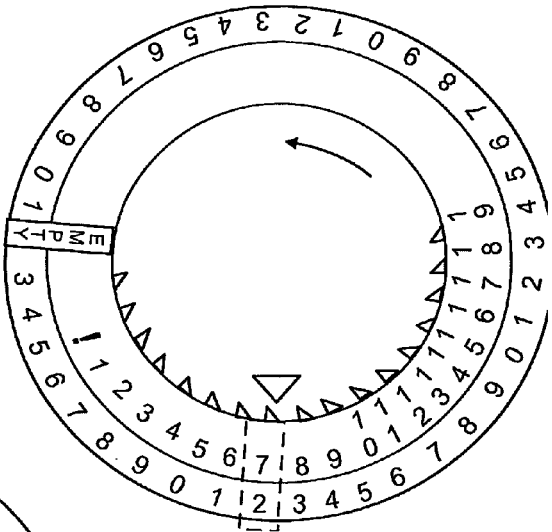
Figure 15C:
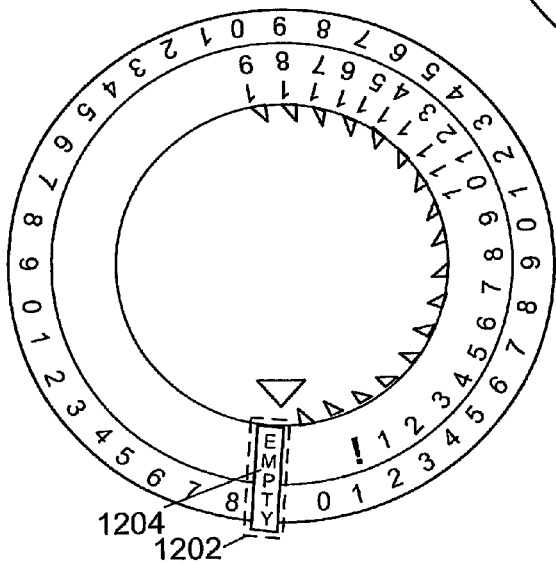

FIG. 15b shows an intermediate count position, in which the number '72' is displayed. In this position, the third row has run out and a blank space appears instead. Alternatively, the blank space may be filled with indicia other than numbers, such as colours.

As the container becomes exhausted, e.g. below ten doses remaining, the second row of numbers can be replaced by an exclamation marks '!' or other warning indicators. Preferred warning indicators for this purpose are colours (e.g. red). Once the final dose has been dispensed (FIG. 15c), a cover element 1204 that is preferably attached to the second ring member and has therefore rotated at the same rate, is aligned with the window 1202. This occludes from view any indicia. The cover may have the word 'EMTPY' written on it for example.

Further actuations of the dispenser may still result in the first ring member 201 being rotated. However, since the teeth are disposed only half way around the second ring member 202, the coupling mechanism can no longer be engaged, i.e. there are no teeth for the slot of the arm to engage with. Thus, no further rotations of the second ring member 202 can be effected, so that the display cover element 1204 remains in place even if the first ring is still rotated by further actuations of the dispenser.

Thus viewed from a still further aspect the present invention provides a ring member for use in a counter having indicia and carrying protrusions that are disposed only partially around said ring member. Preferably the protrusions are disposed on the inner surface of the ring member.

In preferred embodiments the protrusions (e.g. teeth) are equally spaced apart. Particularly preferably the protrusions only extend three quarters of the way (e.g. about 270°) around the ring member, still more preferably the protrusions only extend between a quarter and half way (e.g. about 90°, 108° or 180°, or any angle therebetween) around the ring member.

It will be apparent that the number of deflectors and/or arms (not shown in FIG. 15) will depend on the implemented counting scheme. In FIG. 15 for example, where the first ring member 201 has a first row of numbers comprising four repeated sets of consecutive integers '0' to '9' such that each set covers a quarter turn of the first ring member 201, and where one deflector 1002 is provided, the counter will have four arms spaced at 90 degree intervals. Of course, other configurations will also be possible. For example, where the first ring member 201 has a first row of numbers comprising two repeated sets of consecutive integers '0' to '9' such that each set covers half a turn of the first ring member 201, and where one deflector 1002 is provided, the counter will have two arms spaced at 180 degree intervals. Alternatively, it may be possible to have a single arm and multiple deflectors 1002 spaced at intervals, or multiple arms and deflectors.

Figure 16:
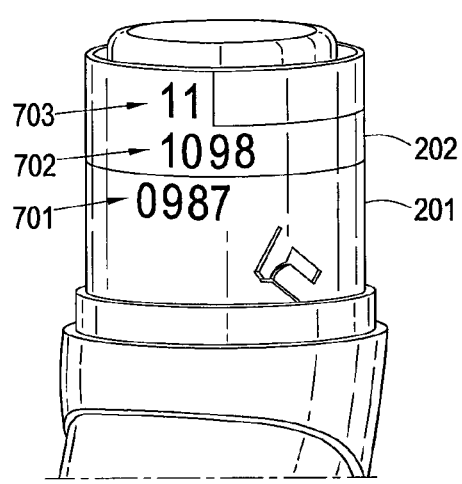
FIG. 16 is a perspective view of a dispenser including a counter according to the present invention.
Figure 17:
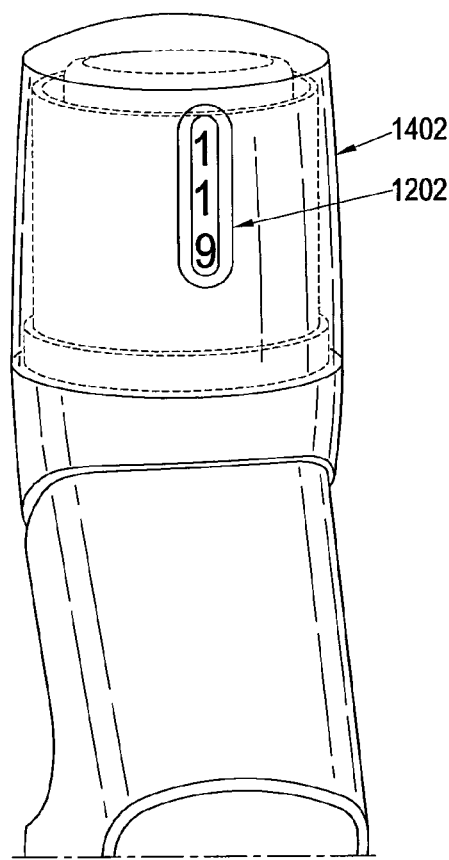
FIG. 17 is a perspective view of a dispenser including a counter according to the present invention.

FIGS. 16 and 17 are perspective views of a dispenser including the counter. In contrast to FIGS. 2 and 3, the pawl-bearing member rather than the teeth-bearing member is integral with the first ring member 201. Also visible in FIG. 16 is a strip of colour following the third row of numbers 703. FIG. 17 shows how a count ('119') can be viewed through a window 1202 of a housing 1402 of the dispenser.

Figure 18A:
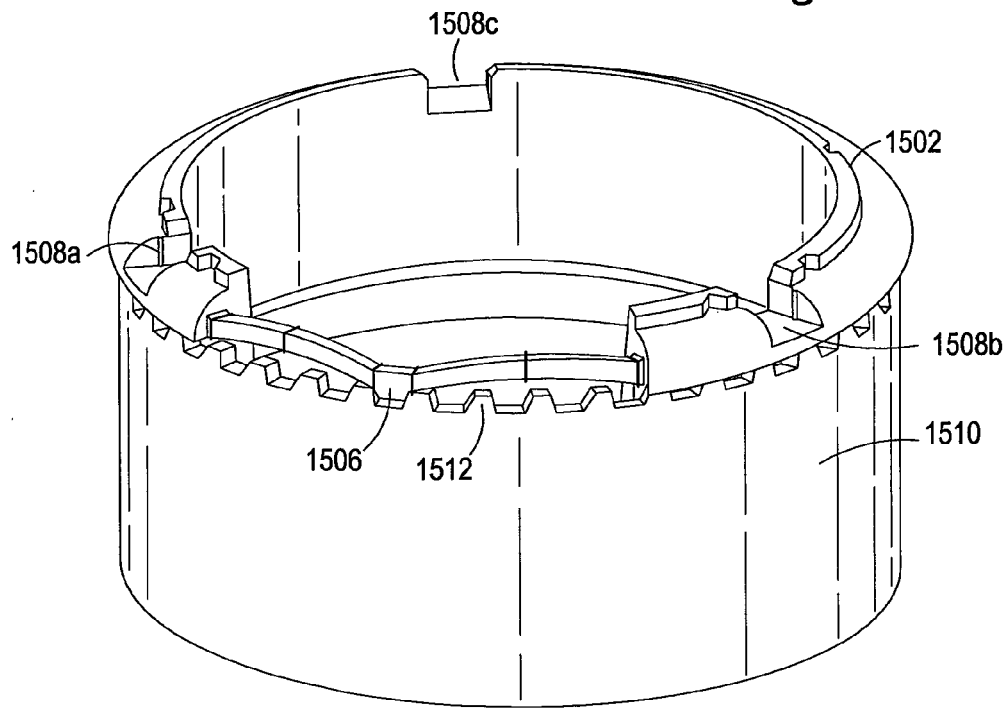
FIGS. 18a to 18c are perspective views of portions of a counter according to the present invention.
Figure 18B:
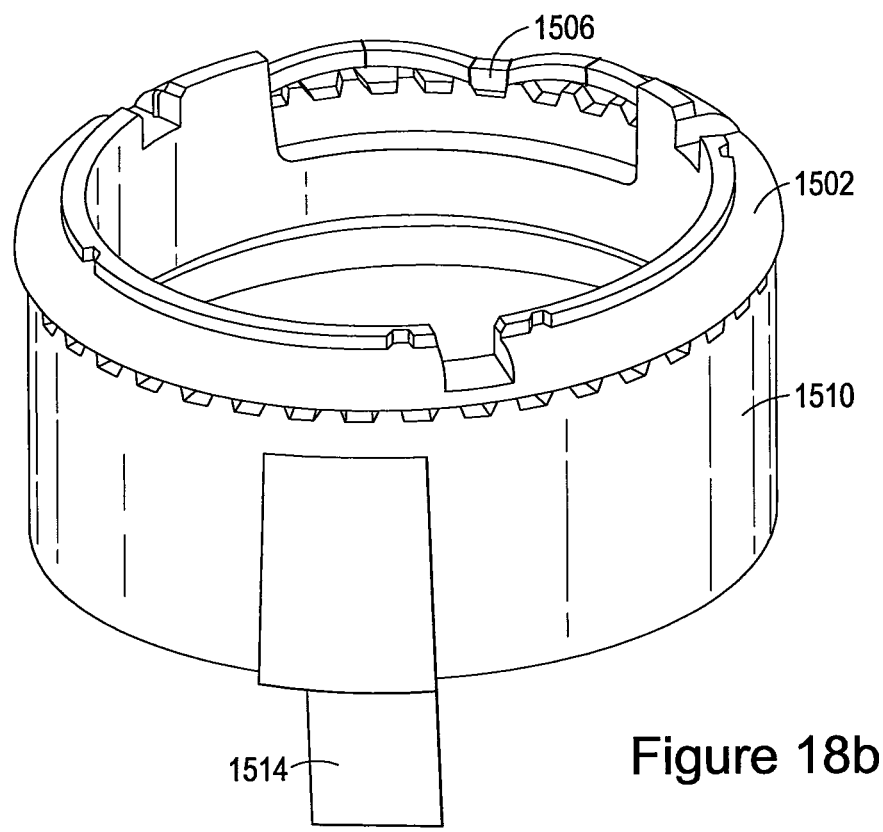
Figure 18C:
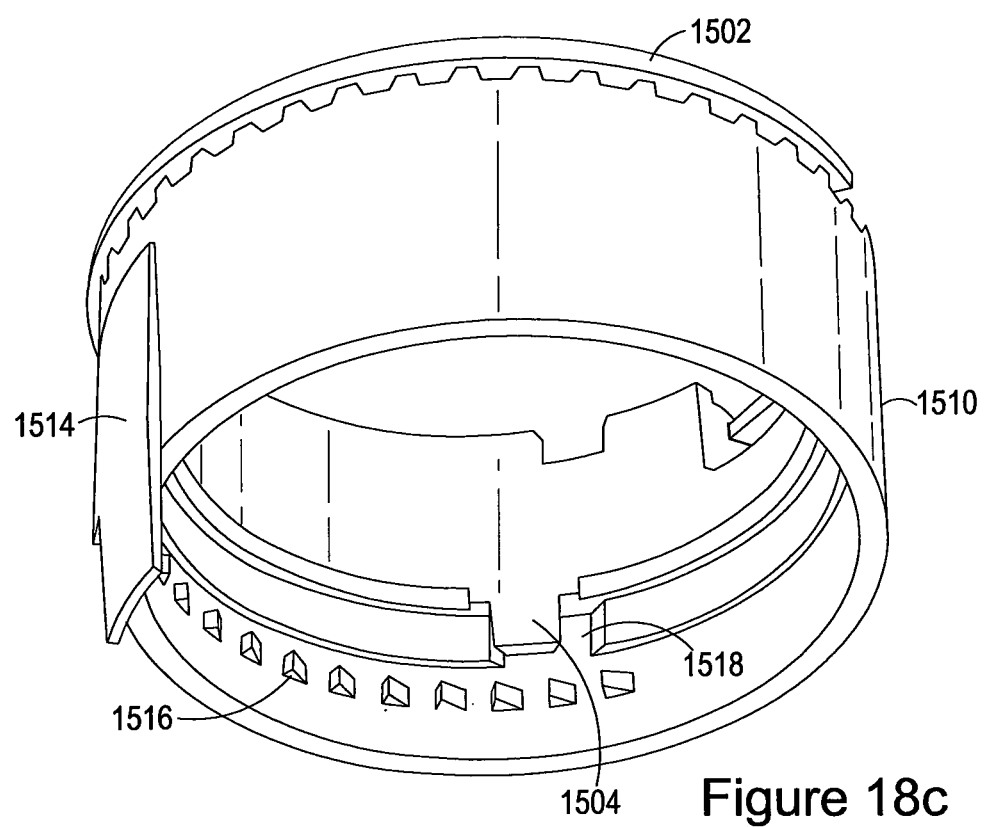

FIGS. 18a to 18c show part of a preferred embodiment of the counter. In this preferred embodiment, the second ring member 1510 is rotatably and coaxially arranged with a first ring member 201 about a central axis 214 as described above (and as shown in FIGS. 10 and 11). For clarity, the first ring member 201 is not shown in these drawings.

As with the embodiments described above, the second ring member is arranged substantially flush on top of the first ring member, with their outer circumferential surfaces being aligned so as to form a substantially continuous surface interrupted only by a hairline where the two ring members meet. A pawl-bearing member 205 of a drive mechanism is integral with the first ring member 201.

In this preferred embodiment, the counter further comprises a third ring member 1502 that is coaxially arranged with the second ring member 1510. In use, the third ring member does not rotate. The third ring member comprises a deflector 1504 to deflect arm 704 on the first ring member 201 to engage with protrusions 1516 on the inside surface of the second ring member 1510 in the manner as described above with reference to FIGS. 13 and 14. As can be seen, the third ring member has a gap 1518 in its outer wall to enable the arm 704 to deflect outwards. A sloped edge on the trailing boundary of the window 1518 engages with an edge of the arm 704 to push the arm 704 away from the teeth 1516 after the arm has engaged with the teeth 1516. This ensures that unwanted further engagement of the tens (second) ring (which would lead to an incorrect dosage value being displayed) does not happen.

The third ring member 1502 further comprises a limiting mechanism 1506 which comprises a flexible and resiliently deformable portion that applies pressure to an upper circumferential surface of the second ring member 1510. The limiting mechanism limits the amount of rotation of the second ring member relative to the third ring member. More specifically, the limiting mechanism prevents the second ring member incorrectly rotating by two protrusions (or counts) in the event that the arm fails to decouple properly. In this embodiment, the second ring member 1510 also comprises a plurality of protrusions 1512 on an upper circumferential surface to engage with the limiting mechanism 1506 of the third ring member 1502. Preferably, protrusions 1512 are substantially equally-spaced. More preferably, the protrusions 1512 have substantially the same spacing as protrusions 1516 on the inside surface of the second ring member.

As described above with reference to FIGS. 13 and 14, when the first and second ring members are coupled, the second ring member rotates at the same rate as the first ring member (until the first and second ring members become uncoupled). By spacing the protrusions 1512 at substantially the same distance as protrusions 1516 (which form part of the coupling mechanism between the first and second ring members), this prevents the second ring member rotating further than is desired even if the arm does not properly decouple, which would indicate an incorrect count.

Furthermore, the third ring member also comprises a plurality of locating recesses 1508a, 1508b and 1508c in the upper circumferential surface. In preferred embodiments, correspondingly-shaped protrusions locate within these recesses to hold the third ring member in place and therefore to prevent rotation of the third ring member. The protrusions may be located in a container or a dispenser (e.g. in a dispenser cap). By preventing the third ring member from rotation, this ensures that the deflector 1504 remains in a consistent position relative to the first and second ring members.

A plurality of corresponding-shaped protrusions located in a container or dispenser may be designed with an asymmetrical pattern to provide a keying function. That is, the third ring member will only locate in one rotational position relative to the container and dispenser, and therefore also the first and second ring members. This ensures that the third ring member is always located correctly with respect to the first and second ring members to allow the count to correctly register.

The second ring member 1510 further comprises a display cover element 1514 for obscuring a view of the first indicia (as described above with reference to FIG. 15) to indicate that the counter has reached zero, indicating an empty dispenser.

Figure 19A:
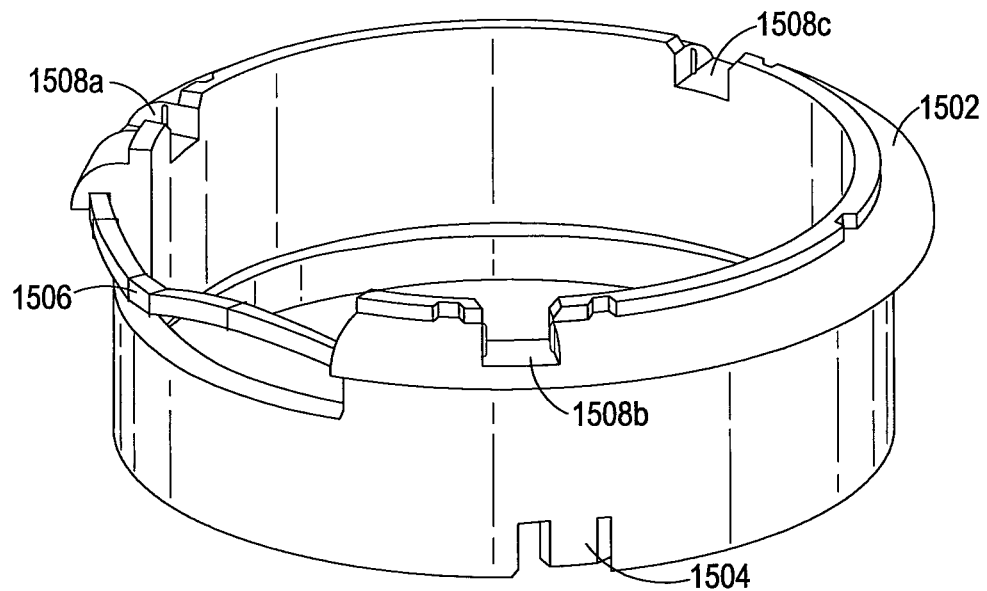
FIGS. 19a to 19b are perspective views of a third ring member of FIG. 18.
Figure 19B:
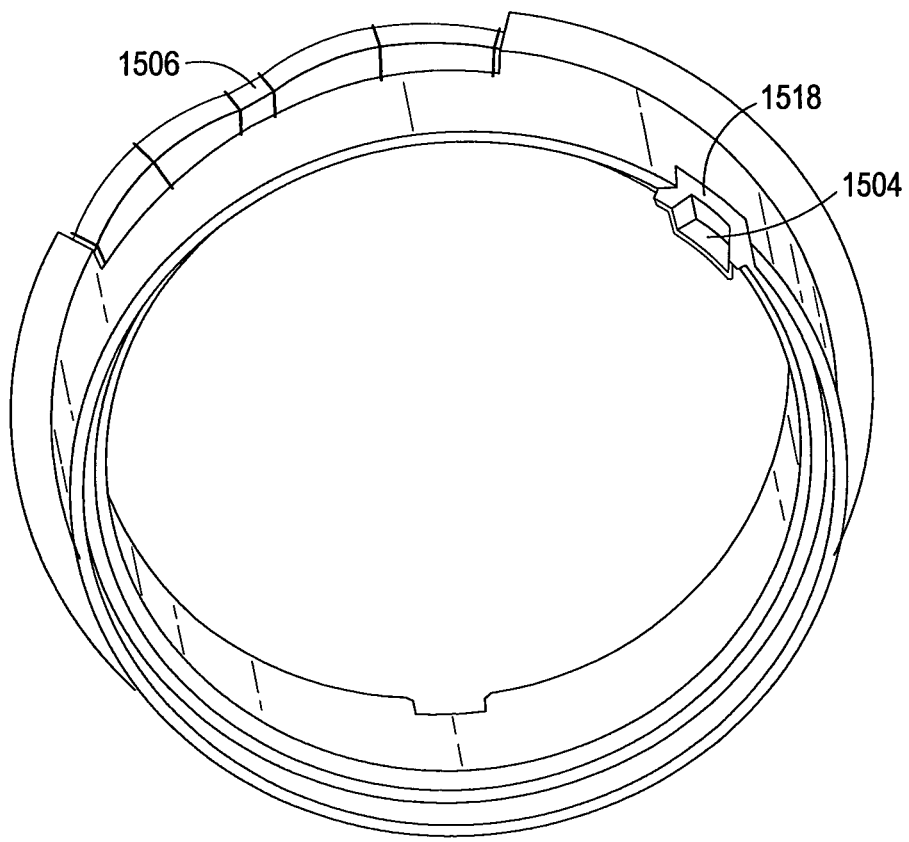

FIGS. 19a and 19b show the third ring member without the second ring member. The reference numerals correspond with those in FIG. 18.

It will be apparent that the third ring member does not comprise indicia, and it is not intended to carry indicia, as this embodiment requires the third ring member to remain in a fixed rotational position relative to the first and second ring members for the count to indicate the correct remaining doses.

While the invention has been exemplified by the above description of specific embodiments, and uses thereof, the foregoing should not be considered by the reader as a limitation on the scope of the invention, which is defined in the appended claims.

The invention claimed is:

1. A counter comprising:
a first ring member having first indicia and a second ring member having second indicia, each of said first and second ring members being rotatable in increments about a common axis, one or both of said first and second indicia indicating a count;
a third ring member being coaxially arranged about said common axis of said first and second ring members;
a drive mechanism for rotating said first ring member; and
a coupling mechanism for releasably coupling said first ring member to said second ring member, to allow said first and second ring members to rotate cooperatively when coupled and to allow independent rotating of said first ring member when not coupled;
wherein said coupling mechanism comprises first and second engagement means and a deflector, said first engagement means being movable radially outwardly and radially inwardly relative to said axis, said first engagement means engage with said second engagement means when said first engagement means are moved radially outwardly and said deflector is connected to, or integral with said third ring member, and deflects said first engagement means radially outwardly.

2. A counter as claimed in claim 1 wherein said first engagement means is deflected radially outwardly after a predetermined degree of rotation of said first ring member, said predetermined amount of rotation of said first ring member being less than a full rotation of said first ring member about said common axis.

3. A counter as claimed in claim 1 wherein said first engagement means is connected to, or integral with, said first ring member.

4. A counter as claimed in claim 1 wherein said first engagement means comprise an arm having a slot and a contact end.

5. A counter as claimed in claim 4 wherein said contact end comprises an upwardly extending component that contacts said deflector.

6. A counter as claimed in claim 4, wherein said first engagement means comprise four arms each having a slot and a contact end.

7. A counter as claimed in claim 1 wherein said second engagement means is connected to, or integral with, said second ring member.

8. A counter as claimed in claim 4 wherein said second engagement means comprises a plurality of protrusions.

9. A counter as claimed in claim 8 wherein said protrusions are equally spaced apart.

10. A counter as claimed in claim 8 wherein when said arm is moved radially outwardly said slot of said arm engages with one of said protrusions.

11. A counter as claimed in claim 1, wherein said third ring member comprises a limiting mechanism to limit free rotation of said second ring member relative to said third ring member about said common axis.

12. A counter as claimed in claim 11, wherein said limiting mechanism comprises a resiliently deformable portion for applying pressure on said second ring member for said limiting.

13. A counter as claimed in claim 11, wherein said second ring member comprises a plurality of substantially equally-spaced protrusions and wherein said limiting mechanism engages with said protrusions for limiting said free rotation of said second ring member.

14. A counter as claimed in claim 1, wherein said third ring member comprises one or more locating recesses disposed in an upper circumferential surface for engaging with correspondingly-shaped protrusions in a housing for preventing free rotation of said third ring member.

15. A dispenser comprising:
a body for receiving a medicament container;
a medicament container;
a dispensing mechanism for dispensing a dose of medicament from said container; and
a counter as claimed in claim 1.

16. A dispenser comprising the counter as claimed in claim 1.

17. A dispenser as claimed in claim 16 which is a pressurised metered-dose inhaler (pMDI).

18. A dispenser as claimed in claim 16, further comprising a tolerance adjustment mechanism.

19. A counter comprising:
a first ring member having first indicia and a second ring member having second indicia, each of said first and second ring members being rotatable in increments about a common axis, one or both of said first and second indicia indicating a count;
a drive mechanism for rotating said first ring member; and
a coupling mechanism for releasably coupling said first ring member to said second ring member, to allow said first and second ring members to rotate cooperatively when coupled and to allow independent rotating of said first ring member when not coupled;
wherein said coupling mechanism comprises first and second engagement means, wherein said first engagement means comprise an arm having a slot and a contact end, said first engagement means are movable radially outwardly and radially inwardly relative to said axis and said first engagement means engage with said second engagement means when said first engagement means are moved radially outwardly.

20. A counter as claimed in claim 19, wherein said coupling mechanism comprises a deflector to deflect said first engagement means radially outwardly.

21. A counter as claimed in claim 20 comprising a third ring member being coaxially arranged about said common axis of said first and second ring members, and wherein said deflector is connected to, or integral with said third ring member.

22. A counter as claimed in claim 21, wherein said third ring member comprises a limiting mechanism to limit free rotation of said second ring member relative to said third ring member about said common axis.

23. A counter as claimed in claim 22, wherein said limiting mechanism comprises a resiliently deformable portion for applying pressure on said second ring member for said limiting.

24. A counter as claimed in claim 22, wherein said second ring member comprises a plurality of substantially equally-spaced protrusions and wherein said limiting mechanism engages with said protrusions for limiting said free rotation of said second ring member.

25. A counter as claimed in claim 21, wherein said third ring member comprises one or more locating recesses disposed in an upper circumferential surface for engaging with correspondingly-shaped protrusions in a housing for preventing free rotation of said third ring member.

26. A counter as claimed in claim 19, wherein said first engagement means is deflected radially outwardly after a predetermined degree of rotation of said first ring member, said predetermined amount of rotation of said first ring member being less than a full rotation of said first ring member about said common axis.

27. A counter as claimed in claim 19 wherein said first engagement means is connected to, or integral with, said first ring member.

28. A counter as claimed in claim 19, wherein said first engagement means comprise four arms each having a slot and a contact end.

29. A counter as claimed in claim 28, wherein said contact end comprises an upwardly extending component that contacts said deflector.

30. A counter as claimed claim 19, wherein said second engagement means is connected to, or integral with, said second ring member.

31. A counter as claimed in claim 19, wherein said second engagement means comprises a plurality of protrusions.

32. A counter as claimed in claim 31, wherein said protrusions are equally spaced apart.

33. A counter as claimed in claim 31, wherein when said arm is moved radially outwardly said slot of said arm engages with one of said protrusions.

34. A dispenser comprising:
a body for receiving a medicament container;
a medicament container;
a dispensing mechanism for dispensing a dose of medicament from said container; and
a counter as claimed in claim 19.

35. A dispenser comprising the counter as claimed in claim 19.

36. A dispenser as claimed in claim 35 which is a pressurised metered-dose inhaler (pMDI).

37. A dispenser as claimed in claim 35, further comprising a tolerance adjustment mechanism.

* * * * *